(12) United States Patent
Iding et al.

(10) Patent No.: US 7,642,366 B2
(45) Date of Patent: Jan. 5, 2010

(54) PHOSPHINE LIGANDS

(75) Inventors: Hans Iding, Rheinfelden (DE); Ernst Kupfer, Zurich (CH); Bruno Lohri, Reinach BL (CH); Kazimierz Michal Pietrusiewicz, Lublin (PL); Kurt Puentener, Basel (CH); Michelangelo Scalone, Birsfelden (CH); Wioleta Swierczynska, Zarzecze (PL); Beat Wirz, Reinach BL (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 254 days.

(21) Appl. No.: 11/591,277

(22) Filed: Nov. 1, 2006

(65) Prior Publication Data
US 2007/0100152 A1 May 3, 2007

(30) Foreign Application Priority Data
Nov. 2, 2005 (EP) .................................. 05110274

(51) Int. Cl.
*C07F 15/04* (2006.01)
(52) U.S. Cl. ....................................................... 556/13
(58) Field of Classification Search ..................... 556/13
See application file for complete search history.

(56) References Cited
FOREIGN PATENT DOCUMENTS
WO WO 03/042135 A2 5/2003

Primary Examiner—Rei-tsang Shiao

(74) *Attorney, Agent, or Firm*—George W. Johnston; Dennis P. Tramaloni

(57) ABSTRACT

The invention is concerned with new phosphine ligands of the formula I

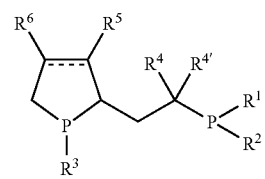

wherein
$R^1$ and $R^2$ are independently of each other alkyl, aryl, cycloalkyl or heteroaryl, said alkyl, aryl, cycloalkyl or heteroaryl may be substituted by alkyl, alkoxy, halogen, hydroxy, amino, mono- or dialkylamino, aryl, $-SO_2-R^7$, $-SO_3^-$, $-CO-NR^8R^{8'}$, carboxy, alkoxycarbonyl, trialkylsilyl, diarylalkylsilyl, dialkylarylsilyl or triarylsilyl;
$R^3$ is alkyl, cycloalkyl, aryl or heteroaryl; $R^{4'}$ and $R^4$ signify independently of each other hydrogen, alkyl or optionally substituted aryl; or $R^{4'}$ and $R^4$ together with the C-atom they are attached to form a 3-8-membered carbocyclic ring; dotted line is absent or is present and forms a double bond; $R^5$ and $R^6$ are independently of each other hydrogen, alkyl or aryl; or linked together to form a 3-8-membered carbocyclic ring or an aromatic ring; $R^7$ is alkyl, aryl or $NR^8R^{8'}$; and $R^8$ and $R^{8'}$ are independently of each other hydrogen, alkyl or aryl;
metal complexes with such ligands as well as the use of such metal complexes as catalysts in asymmetric reactions.

11 Claims, No Drawings

PHOSPHINE LIGANDS

PRIORITY TO RELATED APPLICATIONS

This application claims the benefit of European Application No.05110274.7, filed Nov. 2, 2005, which is hereby incorporated by reference in its entirety.

FIELD OF THE INVENTION

The present invention is concerned with new phosphine ligands, the process to make such ligands, metal complexes of such ligands, as well as the use of such metal complexes as catalysts in asymmetric reactions.

BACKGROUND OF THE INVENTION

Phosphine ligands with chiral centers on carbon and phosphorous atoms are known in the art. A particular class of phosphine ligands is constituted of those linked by a bridge of three carbon atoms, i.e. 1,3-diphosphine ligands. Examples of 1,3-diphosphine ligands with one or two chiral centers on the carbon atoms of the bridge are SKEWPHOS (A) and CHAIRPHOS (B) see *J. Am. Chem. Soc.* 1981, 103, 2273. Another type of chiral phosphine ligands are those where the P atom is contained in a phospholane ring such as for example in the BPE ligand (C), described in *Tetrahedron Asymmetry*, 1991, 2,(7), 569, or in compound D, described in *Angew. Chem. Int. Ed.* 2002, 41(9), 1612.

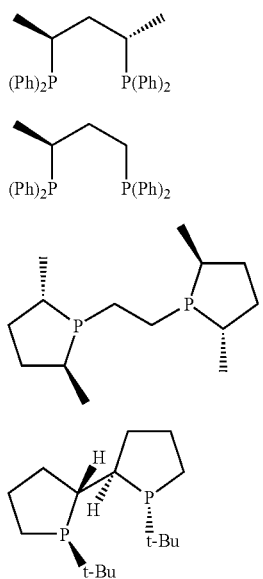

The objective of the present invention is to provide further chiral 1,3-diphosphine ligands with one or two chiral centers on carbon atoms of the bridge and one chiral center on the phosphorus atom, i.e. a new bidentate C,P-chiral 1,3-diphosphine ligand system which form fairly rigid bicyclo[4.3.0]nonane type chelates with transition metals. The process for synthesizing such new ligand is part of the present invention; it has the advantage of being very short as shown in Scheme 1.

SUMMARY OF THE INVENTION

There are provided phosphine ligands of the formula I

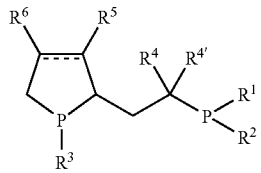

wherein $R^1$, $R^2$, $R^3$, $R^4$, $R^{4''}$, $R^5$ and $R^6$ are hereinafter defined.

DETAILED DESCRIPTION OF THE INVENTION

The invention is therefore concerned with new phosphine ligands of the formula I

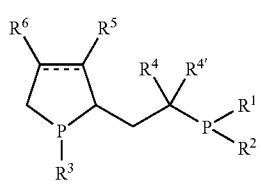

wherein $R^1$ and $R^2$ are independently selected from the group consisting of alkyl, aryl, cycloalkyl and heteroaryl, said alkyl, aryl, cycloalkyl or heteroaryl being unsubstituted or substituted by alkyl, alkoxy, halogen, hydroxy, amino, mono- or dialkylamino, aryl, $-SO_2-R^7$, $-SO_3^-$, $-CO-NR^8R^{8'}$, carboxy, alkoxycarbonyl, trialkylsilyl, diarylalkylsilyl, dialkylarylsilyl or triarylsilyl;

$R^3$ is selected from the group consisting of alkyl, cycloalkyl, aryl and heteroaryl;

$R^{4'}$ and $R^4$ are independently selected from the group consisting of hydrogen, alkyl and aryl; or $R^{4'}$ and $R^4$ together with the C-atom they are attached to form a 3-8-membered carbocyclic ring;

The dotted line is absent or is present and forms a double bond;

$R^5$ and $R^6$ are independently selected from the group consisting of hydrogen, alkyl or aryl; or linked together to form a 3-8-membered carbocyclic ring or an aromatic ring;

$R^7$ is selected from the group consisting of alkyl, aryl and $NR^8R^{8'}$; and $R^8$ and $R^{8'}$ are independently selected from the group consisting of hydrogen, alkyl and aryl.

Compounds of formula I have at least two chiral centers, one on the P atom in the phospholane ring and one on the C2 atom of the phospholane ring as indicated in formula Ia, Ib, Ic and Id.

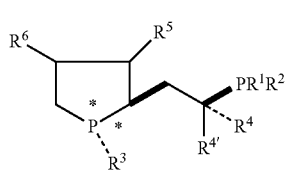

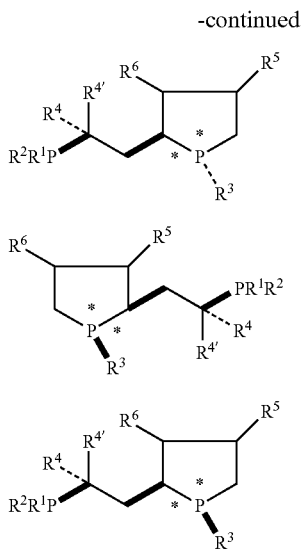

The residues $R^4$, $R^{4'}$, $R^5$ and $R^6$ may form additional chiral centers on the C atom they are attached to and the residues $R^1$ and $R^2$ may form an additional chiral center on the phosphorus atom they are attached to.

The following definitions of the general terms used in the present description apply irrespective of whether the terms in question appear alone or in combination.

The term "alkyl" as used herein signifies straight-chain or branched hydrocarbon groups with 1 to 8 carbon atoms, preferably 1 to 4 carbon atoms such as e.g. methyl, ethyl, propyl, iso-propyl, butyl, iso-butyl and tert-butyl.

Preferably the alkyl groups for $R^1$, $R^2$ and $R^3$ are branched alkyl groups such as iso-propyl, iso-butyl and tert-butyl.

The term "alkoxy" denotes a group wherein the alkyl residue is as defined above, and which is attached via an oxygen atom.

The term "cycloalkyl" stands for 3-to 8-membered rings, such as e.g. cyclopropyl, cyclobutyl, cyclopentyl, cyclohexyl and cycloheptyl, especially for cyclopentyl or cyclohexyl.

Said "alkyl" and "cycloalkyl" groups may be substituted by alkyl (for cycloalkyl), alkoxy, halogen, hydroxy, amino, mono- or dialkylamino, or aryl.

The term "aryl" signifies an aromatic hydrocarbon residue, especially the phenyl residue, which can be unsubstituted or substituted in the ortho-, meta- or para-position or multiply-substituted. Substituents which come into consideration are e.g. phenyl, alkyl or alkoxy groups, preferably methyl or methoxy groups, or amino, monoalkyl- or dialkylamino, preferably dimethylamino or diethylamino, or hydroxy, or halogen such as chlorine, or trialkylsilyl, such as e.g. trimethylsilyl.

Moreover, the term "aryl" can signify naphthyl. Preferred aryl residues are phenyl, tolyl, dimethylphenyl, di-tert-butylphenyl or anisyl.

The term "heteroaryl" signifies a 5- or 6-membered aromatic cycle containing one or more heteroatoms such as S, O and/or N. Examples of such heteroaryl groups are furyl, thienyl, benzofuranyl or benzothienyl.

ABBREVIATIONS

BARF tetrakis[3,5-bis(trifluoromethyl)phenyl]borate
c concentration
cod (Z,Z)-1,5-cyclooctadiene
conv. conversion
DABCO 1,4-diazabicyclo[2.2.2]octane
DBU 1,8-diazabicyclo(5,4,0)undec-7-ene
DEAD diethyl azodicarboxylate
DIAD diisopropyl azodicarboxylate
ee enantiomeric excess
EI-MS: electron impact mass spectroscopy
EtOAc ethyl acetate
EtOH: ethanol
GC: gas chromatography
h hour
HPLC: high performance liquid chromatography
HV: high vacuum
m.p. melting point
MS: mass spectroscopy
Me-PEP 2-(2-diphenylphosphino-2-methyl)ethyl-1-phenylphospholane
PEP 2-(2-diphenylphosphino)ethyl-1-phenylphospholane
PMP5 2-[(diphenylphosphino)methyl]-1-phenyl-phospholane
S/C molar substrate-to-catalyst ratio
TBME: tert-butyl methyl ether
TFA: trifluoroacetic acid
THF tetrahydrofuran For the denotation of cis- and trans configuration in the compounds of the invention and of related compounds the convention depicted below is adhered to:

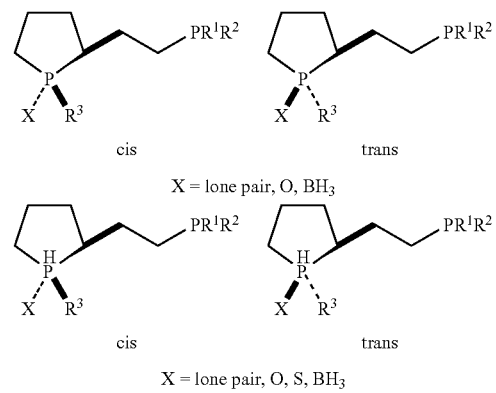

Preferred compounds of formula I are those of formula

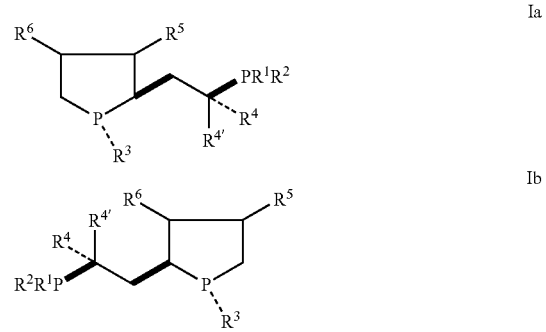

wherein $R^1$, $R^2$, $R^3$, $R^4$, $R^{4'}$ $R^5$, $R^6$, $R^7$, $R^8$ and $R^{4'}$ are as defined above.

Other preferred compounds have the formula

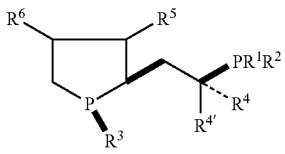

Ic

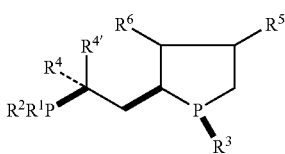

Id wherein $R^1$, $R^2$, $R^3$, $R^4$, $R^{4'}$, $R^5$, $R^6$, $R^7$, $R^8$ and $R^{4'}$ are as defined above.

Still other preferred compounds have the formula

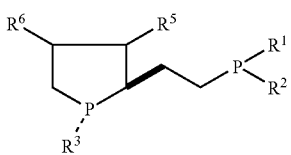

Ie

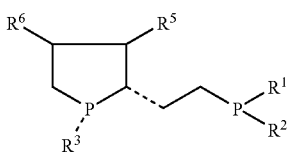

If wherein $R^1$, $R^2$, $R^3$, $R^5$, $R^6$, $R^7$, $R^8$ and $R^{4'}$ are as defined above.

One embodiment of the invention is compounds of formula I wherein $R^1$ and $R^2$ are alike and signify alkyl, aryl, cycloalkyl or heteroaryl, said alkyl, aryl, cycloalkyl or heteroaryl may be substituted by alkyl, alkoxy, halogen, hydroxy, amino, mono- or dialkylamino, aryl, —$SO_2$—$R^7$, —$SO_3^-$, —CO—$NR^8R^{8'}$, carboxy, alkoxycarbonyl, trialkylsilyl, diarylalkylsilyl, dialkylarylsilyl or triarylsilyl;

$R^3$ is $C_{1-4}$ alkyl or aryl;

$R^{4'}$ and $R^4$ are independently of each other hydrogen, $C_{1-4}$ alkyl or aryl;

$R^5$ and $R^6$ are independently of each other hydrogen, $C_{1-4}$ alkyl or phenyl;

the dotted line is absent; and $R^7$, $R^8$ and $R^{8'}$ are as defined above.

Another embodiment of the invention is compounds of formula I, wherein $R^1$ and $R^2$ are alike and signify aryl;

$R^3$ is tert-butyl or phenyl;

$R^{4'}$ and $R^4$ are independently of each other hydrogen, $C_{1-4}$ alkyl or aryl;

$R^5$ and $R^6$ are hydrogen; and the dotted line is absent.

Another embodiment of the invention is compounds of formula I, wherein $R^1$ and $R^2$ are alike and signify aryl;

$R^3$ is phenyl;

$R^4$, $R^{4'}$ are independently of each other hydrogen, methyl or phenyl;

$R^5$ and $R^6$ are hydrogen; and the dotted line is absent.

Another embodiment of the invention is compounds of formula I, wherein $R^1$ and $R^2$ are alike and signify phenyl;

$R^3$ is phenyl;

$R^4$, $R^{4'}$ are independently of each other hydrogen, methyl or phenyl;

$R^5$ and $R^6$ are hydrogen; and the dotted line is absent.

Another embodiment of the invention is compounds of formula Ie or If, wherein $R^1$ and $R^2$ are alike and signify alkyl, aryl, cycloalkyl or heteroaryl, said alkyl, aryl, cycloalkyl or heteroaryl may be substituted by alkyl, alkoxy, halogen, hydroxy, amino, mono- or dialkylamino, aryl, —$SO_2$—$R^7$, —$SO_3^-$, —CO—$NR^8R^{8'}$, carboxy, alkoxycarbonyl, trialkylsilyl, diarylalkylsilyl, dialkylarylsilyl or triarylsilyl;

$R^3$ is $C_{1-4}$ alkyl or aryl;

$R^5$ and $R^6$ are independently of each other hydrogen, $C_{1-4}$ alkyl or phenyl;

the dotted line is absent; and $R^7$, $R^8$ and $R^{8'}$ are as defined above.

Another embodiment of the invention is compounds of formula Ie or If, wherein $R^1$ and $R^2$ are alike and signify aryl;

$R^3$ is ter-butyl or phenyl;

$R^5$ and $R^6$ are hydrogen; and the dotted line is absent.

Another embodiment of the invention is compounds of formula Ie or If, wherein $R^1$ and $R^2$ are alike and signify phenyl;

$R^3$ is phenyl;

$R^5$ and $R^6$ are hydrogen; and the dotted line is absent.

Still another embodiment of the invention is compounds of formula I, which compounds are:

($S_P$,R)-trans-2-(2-Diphenylphosphino)ethyl-1-phenylphospholane;

($S_P$,S)-cis-2-(2-diphenylphosphino)ethyl-1-phenylphospholane;

($S_P$,R,R)-trans-2-(2-diphenylphosphino-2-methyl)ethyl-1-phenylphospholane;

($S_P$,R,S)-trans-2-(2-diphenylphosphino-2-methyl)ethyl-1-phenylphospholane;

($R_P$,R,R)-cis-2-(2-diphenylphosphino-2-methyl)ethyl-1-phenylphospholane;

($R_P$,R,S)-cis-2-(2-diphenylphosphino-2-methyl)ethyl-1-phenylphospholane;

($S_P$,R,R)-trans-2-(2-diphenylphosphino-2-phenyl)ethyl-1-phenylphospholane;

($S_P$,R,S)-trans-2-(2-diphenylphosphino-2-phenyl)ethyl-1-phenylphospholane;

($R_P$,R,R)-cis-2-(2-diphenylphosphino-2-phenyl)ethyl-1-phenylphospholane; or ($R_P$,R,S)-cis-2(2-diphenylphosphino-2-phenyl)ethyl-1-phenylphospholane; or the enantiomers of these compounds The ligands of formula I are prepared according to the following reaction schemes:

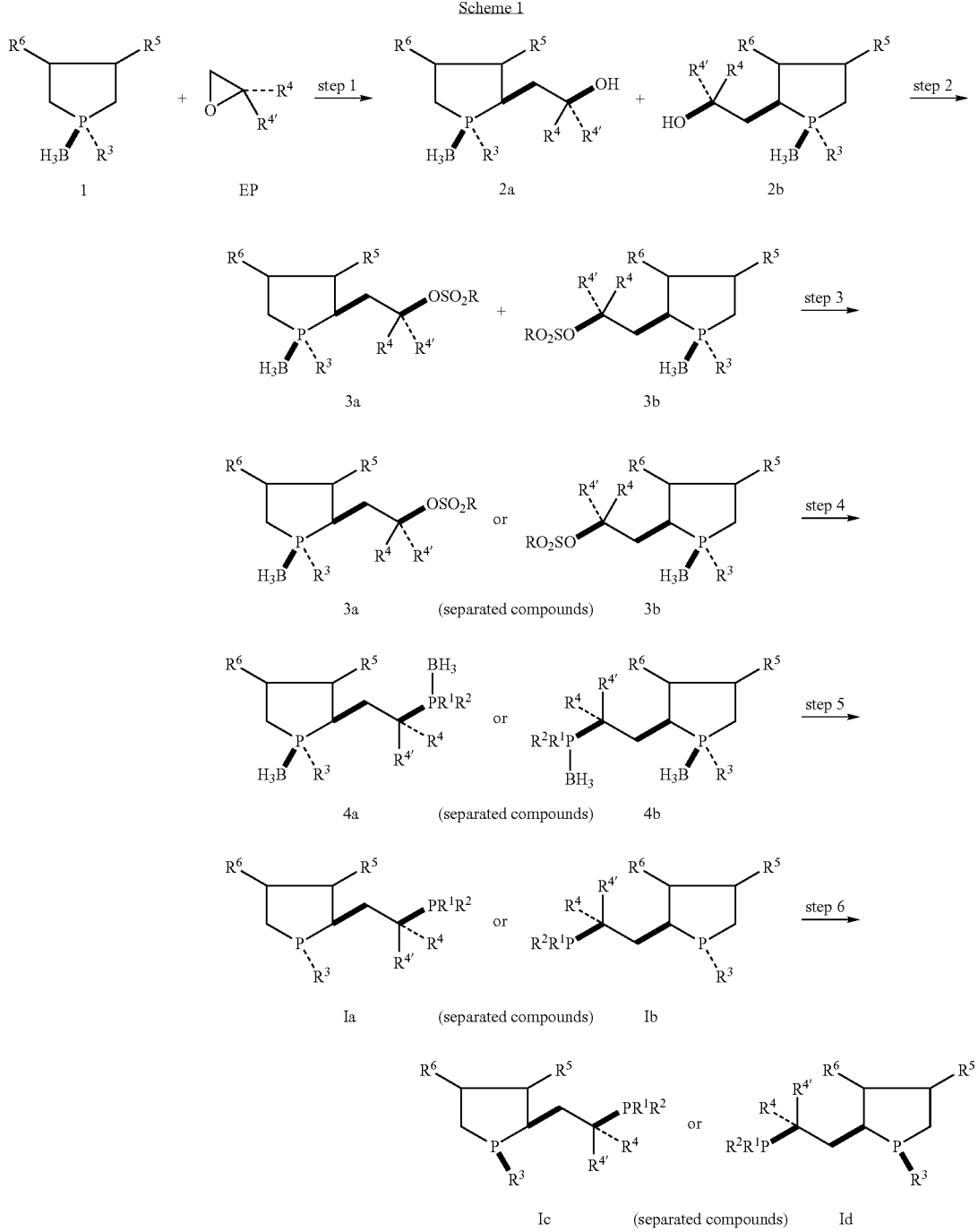

Scheme 1

Step 1

The phospholane borane complex 1 is metallated with a metallation reagent, such as an aryl or alkyl lithium reagent or a lithium amide reagent and subsequently reacted with a non-chiral epoxide EP, such as ethylene oxide or isobutylene oxide, or with an optically active epoxide, such as (R)- or (S)-propylene oxide, (R)- or (S)-styrene oxide or similar epoxides to give trans-2-hydroxyethyl-phospholanes as a mixture of isomers 2a and 2b. Metallation reagents may be phenyl-butyl-, sec- and tert-butyllithium or the like, or lithium-di-iso-propylamide, lithium-2,2,6,6,-tetramethylpiperidide or the like. The metallation may take place in the presence of a complexing agent such as N,N,N',N'-tetramethyl-ethylene-diamine, sparteine or the like. In a preferred version sec-butyllithium is used as the metallation reagent in the presence of (−)-sparteine.

Step 2

The mixture of isomeric trans-2-hydroxyethyl-phospholanes 2a and 2b is converted to a corresponding mixture of sulfonates 3a and 3b according to general procedures well known in the literature, e.g. in the case of R=CH$_3$ by reaction with mesyl anhydride or chloride and a base in an organic solvent. Sulfonates with R=alkyl (e.g. methyl or ethyl) and R=aryl (e.g. p-tolyl, p-nitrophenyl, p-bromophenyl) and the like are prepared in this way. In a preferred version mesyl anhydride is used as the reagent in the presence of Hünig's base in dichloromethane to give a mixture of sulfonates 3a and 3b (R=CH$_3$).

Step 3

Diastereomerically and enantiomerically pure sulfonates 3a and 3b are isolated either by a crystallization procedure or by another separation method such as preparative HPLC. Each of compounds 3a and 3b is then separately carried through step 4 to step 6 as depicted in Scheme 1 and described below.

Step 4

The sulfonates 3a and 3b are each separately treated with a phosphine R$^1$R$^2$PH in the presence of a base, such as t-BuOK, t-BuONa, n-BuLi, NaH or the like in an organic solvent. The residues in the phosphine R$^1$R$^2$PH are as defined above for formula I. The reaction mixture is then treated with a borane delivering agent, such as e.g. the borane-tetrahydrofuran complex, the borane-N,N-diethylaniline complex, the borane-dimethysulfide complex or the like to give the desired diphosphines as the bis-borane complexes 4a and 4b. In a preferred version the sulfonate 3a or 3b (R=CH$_3$) is reacted with a phosphine R$^1$R$^2$PH in the presence of t-BuOK as the base in tetrahydrofuran as the solvent, followed by treatment with borane-tetrahydrofuran complex to give the bis(borane) complex 4a or 4b.

Step 5

The deboronation is achieved by treatment of the bis(borane) adducts 4a and 4b with an amine base such as e.g., 1,4,-diazabicyclo[2.2.2]octane (DABCO), pyrrolidine, diethylamine or the like or by treatment with an acid such as HBF$_4$ or the like in an organic solvent to give the free 1,3-diphosphines Ia and Ib. In a preferred version the diphosphines Ia and Ib are obtained from the bis(borane) adducts 4a and 4b by treatment with DABCO in toluene.

Step 6

The cis-configurated diphosphines Ic and Id are obtained on treatment of the trans-configurated diphosphines Ia and Ib at elevated temperatures in an organic solvent.

In a preferred version, Ia or Ib is heated in xylene to 180-250° C., preferably 210° C.

The separation of the isomers has been described to occur in Step 3 at the stage of the sulfonates. It has to be understood, that within the present invention, the separation of the isomers can also take place at another stage of the synthesis using conventional methods such as crystallization, flash chromatography or preparative HPLC or the like. In this way, e.g. the isomers 2a and 2b can be separated after carrying out the reaction described under Step 1 or, alternatively e.g. the isomers 4a and 4b can be separated after carrying out the reaction described under Step 4. It is clear, that in these cases the procedure described under Step 3 can be omitted.

In a variation of the synthesis depicted in Scheme 1, steps 1 to 3 can be replaced by an analogous reactions sequence starting from a phospholane-1-sulfide as shown in Scheme 1a. Phospholane-1-sulfide compounds 1' are known and can be prepared according to Baccolini, B.; Boga C.; Negri, U. *Synlett* 2000, 1685.

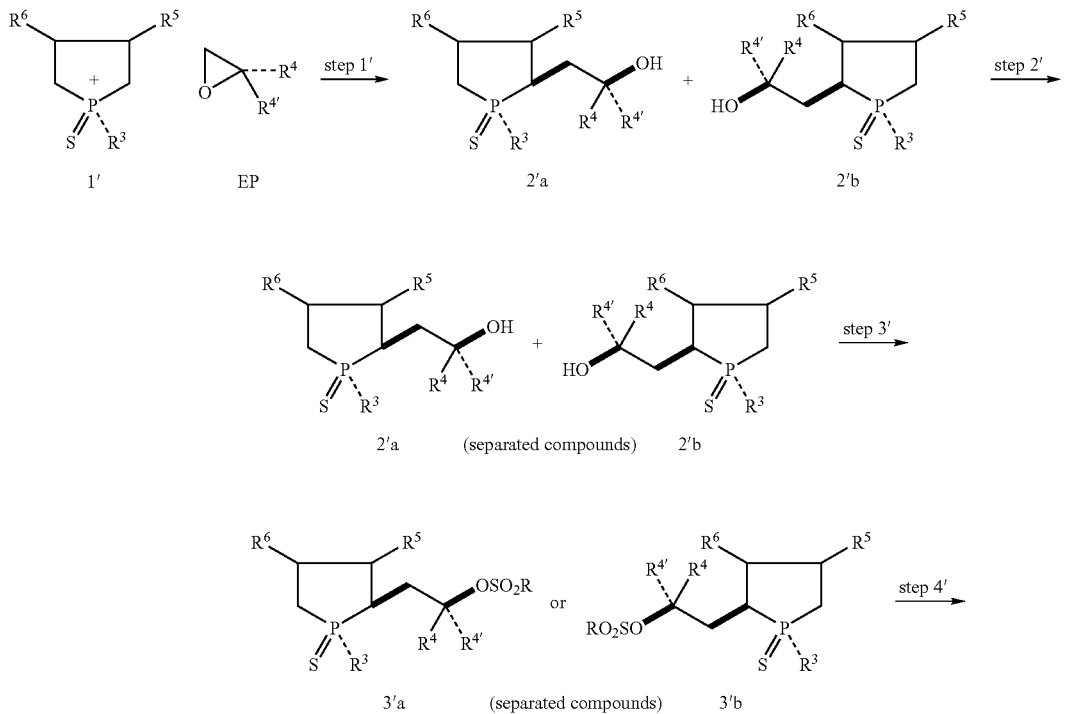

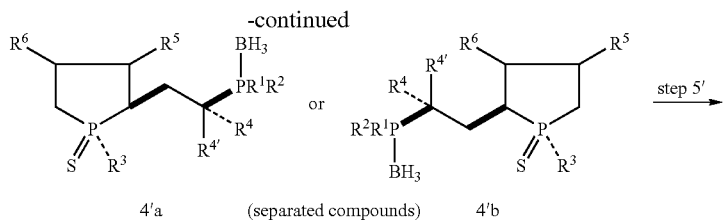

Step 1'

The phospholane-1-sulfide 1' is metallated as e.g. described by Tang W.; Zhang, X. *Angew. Chem. Int. Ed.* 2002, 41, 1612, with a metallation reagent, such as an aryl or alkyl lithium reagent or a lithium amide reagent and subsequently reacted with a non-chiral epoxide EP, such as ethylene oxide or isobutylene oxide, or with an optically active epoxide, such as (R)- or (S)-propylene oxide, (R)- or (S)-styrene oxide or similar epoxides to give trans-2-hydroxyethyl-phospholanes as a mixture of isomers 2a and 2b. Metallation reagents may be phenyl-butyl-, sec- and tert-butyllithium or the like, or lithium-di-iso-propylamide, lithium-2,2,6,6,-tetramethylpiperidide or the like. The metallation may take place in the presence of a complexing agent such as N,N,N',N'-tetramethyl-ethylene-diamine, sparteine or the like. In a preferred version sec-butyllithium is used as the metallation reagent in the presence of (−)-sparteine.

Step 2'

Diastereomerically pure alcohols 2'a and 2'b are isolated either by a crystallization procedure or by another separation method such as preparative HPLC. Each of compounds 2'a and 2'b is then separately carried through the subsequent steps as depicted in Scheme 1a and described below.

Step 3'

The isomeric trans-2-hydroxyethyl-phospholanes 2'a and 2'b are each separately converted to the corresponding sulfonates 3'a and 3'b according to general procedures well known in the literature, e.g. in the case of R=$CH_3$ by reaction with mesyl anhydride or chloride and a base in an organic solvent. Sulfonates with R=alkyl (e.g. methyl or ethyl) and R=aryl (e.g. p-tolyl, p-nitrophenyl, p-bromophenyl) and the like are prepared in this way. In a preferred version mesyl chloride is used as the reagent in the presence of triethylamine in diethyl ether to give the sulfonates 3'a and 3'b (R=$CH_3$). Sulfonates obtained in this way can either be isolated or without isolation directly be treated with a phosphine as described in Step 4'.

Step 4'

The sulfonates 3'a and 3'b are each separately treated with a phosphine $R^1R^2PH$ in the presence of a base, such as t-BuOK, t-BuONa, n-BuLi, NaH or the like in an organic solvent. The residues in the phosphine $R^1R^2PH$ are as defined above for formula I. The reaction mixture is then treated with a borane delivering agent, such as e.g. the borane-tetrahydrofuran complex, the borane-N,N-diethylaniline complex, the borane-dimethysulfide complex or the like to give the desired borane complexes 4'a and 4'b. In a preferred version the sulfonate 3'a or 3'b (R=$CH_3$) is reacted in diethyl ether/tetrahydrofuran as the solvent mixture with a phosphine $R^1R^2PH$ previously deprotonated using n-BuLi as the base, followed by treatment with borane-tetrahydrofuran complex to give the borane complex 4'a or 4'b.

Step 5'

The borane complexes 4'a and 4'b are each separately treated with a reducing agent, such as $LiAlH_4$, Na, Li, $PBu_3$, $Si_2Cl_6$ or the like in an organic solvent, in order to remove the sulfur group. The resulting diphosphine-monoborane complexes are then converted into the bis-borane complexes 4a and 4b using a borane delivering agent of the type mentioned above. In a preferred version, the sulfur group in 4'a and 4'b is removed using $Si_2Cl_6$ as the reagent and the bis-borane 4a and 4b is formed using borane-tetrahydrofuran complex as the reagent.

The bis-borane 4a and 4b are then each Separately Converted to the Diphosphines Ia and Ib as Depicted in Scheme 1.

In a further variation of the synthesis depicted in Scheme 1, steps 1 to 3 can be replaced in analogy to the way described in Scheme 1' while compound 1' which is metallated and reacted with an epoxide is not a phospholane-1-sulfide but a phospholane-1-oxide. Metallation of a phosphine oxide of this type is described in US 2004/0110975. The phosphine oxide group in the compound corresponding to 4'a and 4'b can be converted to obtain bis-borane 4a and 4b using conditions as described below for the conversion of compound to 12 in Scheme 2, Step 7.

The Compounds of Formula I, wherein $R^4$ and $R^{4'}$ are Hydrogen can be Prepared Alternatively According the Reaction Schemes 2 and 3:

The synthesis depicted in scheme 2 is described as follows. The starting material, cis-hydroxy compound 5 is synthesized according to Bodalski, R.; Janecki, T.; Glowka, M. *Phosphorus and Sulfur* 1982, 14, 15.

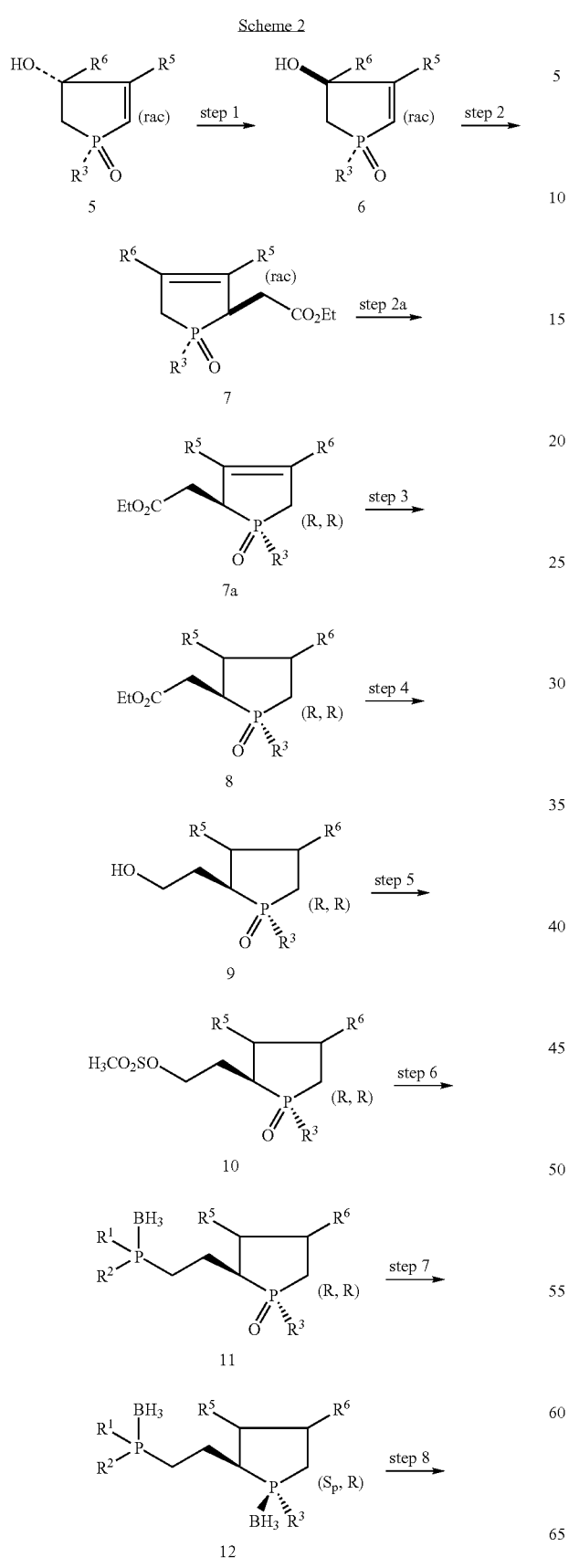

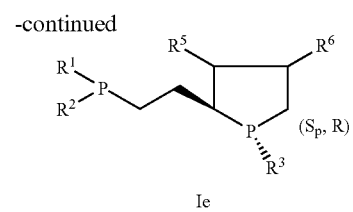

Ie

Step 1

The trans-hydroxy intermediate (6) is synthesized from the cis one by the Mitsunobu inversion of its carbinol centre (Mitsunobu, O.; Yamada, M. *Bull. Chem. Soc., Jpn.,* 1967, 40, 2380). Diisopropylazadicarboxylate (DIAD) is used instead of diethyl azodicarboxylate (DEAD) and after hydrolysis of the ester intermediate the compound 6 is obtained. In a preferred version, diisopropyl azodicarboxylate (DIAD) is used in the presence of 3,5-dinitrobenzoic acid, and the intermediate 3,5-dinitrobenzoate is cleaved to compound 6 using $K_2CO_3$ in an alcohol, such as methanol or ethanol.

Step 2

The compound 7 is synthesized as a racemate by using hydroxyphospholanes 6 as substrate and by employing the ortho ester variant of the rearrangement (Claisen-Johnson) (Johnson, W. S; Brocksom, T. J.; Loew, P.; Rich, D. H.; Werthemann, R. A.; Arnold, R. A.; Li, T.; Faulkner, D. J. *J. Am. Chem. Soc.* 1970, 92, 4463) involving heating of 6 with excess of ethyl orthoacetate in the presence of a weak acid, such as propionic acid.

Step 2a

The optically active compound 7a is obtained by an enzymatic resolution of the racemic compound 7 using an enzyme, such as an esterase. In a preferred version, rac-7 is enzymatically hydrolyzed at pH 7.0 in the presence of ThermoCat Esterase E020 (ThermoGen, USA) to leave, after approx. 50% conversion, the desired ester 7a which is isolated in >99.5% ee as the (R,R) enantiomer. The co-produced corresponding (S,S)-acid (>99.5% ee) can be transformed into an alkyl ester using a method known in the art. The thus prepared ester can be used to complete the analogous synthesis (step 3 to step 8) in the (S,S) series, which is depicted in Scheme 2 and described hereafter for the (R,R)-series.

Step 3

The double bond in the 5-membered ring of 7 is hydrogenated over a hydrogenation catalyst, such as a Pd/C catalyst to give ester 8.

Step 4

The ester 8 is reduced to the corresponding alcohol 9 by treatment with a reducing agent, such as sodium borohydride or lithium aluminum hydride in an organic solvent, such as in THF. In a preferred version, the ester 8 is reduced with sodium borohydride in THF-MeOH.

Step 5

The hydroxyl group in 9 is converted into a mesyloxy group by treatment with methanesulfonic anhydride in the present of a base. In a preferred version, the reaction is carried out in the presence of N-ethyldiisopropylamine as a base, which allows pure trans diastereoisomer 10 to be obtained.

Step 6

The nucleophilic displacement of the mesyloxy group in 10 by lithium diphenylphosphide followed by addition of an organic solution of $BH_3$, such as $BH_3$ in THF, leads to the corresponding borane-protected adduct 11.

Step 7

Stereoretentive reduction of the phosphine oxide group of compound 11 with phenylsilane and treatment of the resulting phosphine with an organic solution of $BH_3$, such as 1M $BH_3$ in THF lead to diastereomerically pure diphosphine diborane adduct 12.

Step 8

Finally, the conversion of diphosphine diborane 12 into the desired diphosphine Ie can be readily and stereoselectively achieved by using DABCO in benzene (cf. Imamoto, T.; Tsuruta, H.; Wada, Y,; Masuda, H.; Yamaguchi, K. *Tetrahedron Lett*. 1995, 36, 8271).

In the synthesis depicted in Scheme 3, the optically active starting material 2-methylenephospholane-1-oxide (13) is prepared according to WO 2004/050669.

Phosphinothioylacetic acid tert-butyl ester (14), the other starting material, is prepared as follows and as described in the experiment part of this application:

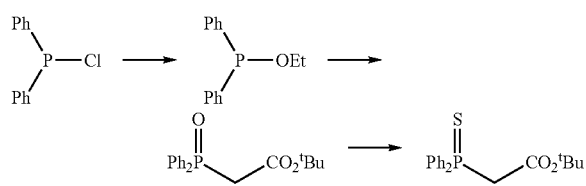

The synthesis depicted in Scheme 3 is described as follows.

Scheme 3

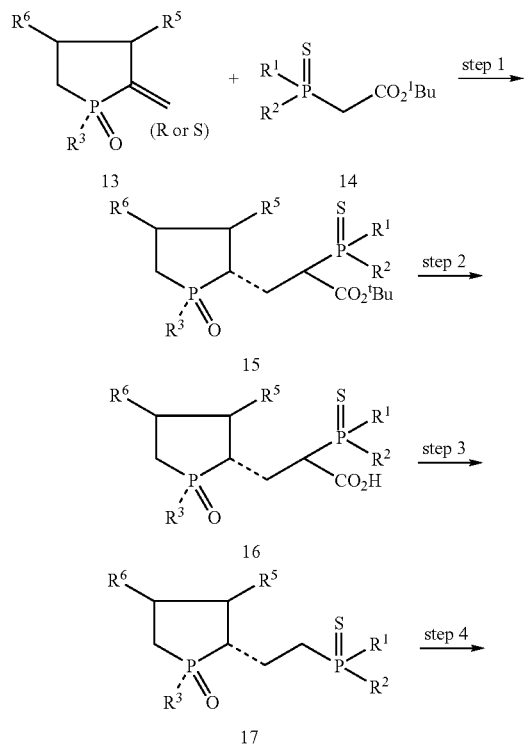

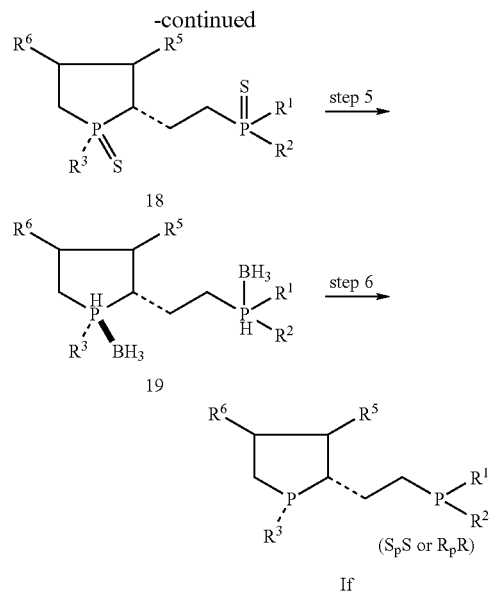

Step 1

2-Methylene-phospholane 1-oxide 13 and phosphinothioyl acetate 14 are dissolved in an organic solvent, such as benzene. The resulting mixture is treated with a base, such as NaH to obtain the desired adduct 15.

Step 2

The tert-butyl group is removed by treatment of adduct 15 with an acid, such as formic acid to obtain acid 16.

Step 3

Decarboxylation of acid 16 in the presence of $Cu_2O$ and an organic base, such as pyridine leads to monoxide-monosulfide 17.

Step 4

The phosphine oxide group in monoxide-monosulfide 17 is reduced with retention of configuration by a reducing agent, such as phenylsilane and converted into the corresponding diphosphine-disulfide 18 by treatment with sulfur.

Step 5

Desulfurisation of the disulfide 18 with hexachlorodisilane ($Si_2CL_6$) (cf. Zon, G.; DeBuin, K. E.; Naumann, K.; Mislow, K. *J. Am. Chem. Soc*. 1969, 91, 7023) with retention of configuration leads to the corresponding diphosphine which is transformed in situ into the corresponding diphosphine diborane 19, using an organic solution of $BH_3$, such as 1M $BH_3$ in THF.

Step 6

The conversion of diphosphine diborane 19 into the desired diphosphine If is stereoselectively achieved by using DABCO in an organic solvent, such as toluene (cf. Imamoto, T.; Tsuruta, H.; Wada, Y,; Masuda, H.;Yamaguchi, K. *Tetrahedron Lett*. 1995, 36, 8271).

The optically active ligands of formula I form complexes with transition metals, especially with transition metals of Group VIII, such as ruthenium, rhodium, iridium, palladium and nickel. These complexes can be used as catalysts in asymmetric reactions such as hydrogenations and enantioselective hydrogen displacements in prochiral allylic systems.

Preferably the metal complexes are used in their isolated forms for the hydrogenations. Alternatively, the complexes may be prepared in situ.

These catalysts, i.e. the complexes of a transition metal and the chiral diphosphine ligands of formula I, are novel and are likewise an object of the present invention.

The aforementioned transition metal complexes, especially the complexes with metals of group VIII can be represented e.g. by the following formula II and III indicated below:

  II wherein
M stands for a transition metal,
L stands for the diphosphine compound of formula I;

wherein
X is a coordinating anion such as e.g. Cl, Br or I
m, n and p are each 1, and
q is 0, if M is Rh;

or
X is acyloxy, such as e.g. acetoxy, trifluoroacetoxy or pivaloyloxy,
m and n are each 1,
p is 2, and
q is 0, if M is Ru;

or
X is Cl,
m and n are each 2,
p is 4,
q is 1, and
A is triethylamine, if M is Ru;

or
X is a π-methallyl group,
m and n are each 1,
p is 2, and
q is 0, if M is Ru;

or
X is a coordinating anion such as e.g. Cl, Br or I,
m, n and p are each 1, and
q is 0, if M is Ir;

or
X is Cl,
m and n are each 1,
p is 2, and
q is 0, if M is Pd;

or
X is Cl, Br or I,
m and n are each 1,
p is 2, and
q is 0, if M is Ni.

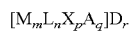  III wherein
M stands for a transition metal, and
L stands for the diphosphine compound of formula I;

wherein
X is a diene ligand such as cod or nbd,
D is a non-coordinating anion such as e.g. $BF_4$, $ClO_4$, $PF_6$, $SbF_6$, $CF_3SO_3$, $BPh_4$, or BARF,
m, n, p and r are each 1, and
q is 0, if M is Rh;

or
X is an olefinic ligand such as e.g. cyclooctene or ethylene,
D is a non-coordinating anion such as e.g. $BF_4$, $ClO_4$, $PF_6$, $SbF_6$, $CF_3SO_3$, $BPh_4$, or BARF,
m, n and r are each 1,
p is 2 and
q is 0, if M is Rh;

or
X is Cl, Br or I,
A is benzene p-cymene,
D is Cl, Br or I, and
m, n, p, q and r are each 1, if M is Ru;

or
D is a non-coordinating anion such as e.g. $BF_4$, $ClO_4$, $PF_6$, $SbF_6$, $CF_3SO_3$, $BPh_4$, or BARF,
m and n are each 1,
p and q are each 0, and
r is 2, if M is Ru;

or
X is a diene ligand such as cod or nbd,
D is a non-coordinating anion such as e.g. $BF_4$, $ClO_4$, $PF_6$, $SbF_6$, $CF_3SO_3$, $BPh_4$, or BARF,
m, n, p and r are each 1, and
q is 0, if M is Ir;

or
X is an olefinic ligand such as e.g. cyclooctene or ethylene,
D is a non-coordinating anion such as e.g. $BF_4$, $ClO_4$, $PF_6$, $SbF_6$, $CF_3SO_3$, $BPh_4$, or BARF,
m, p and r are each 1,
n is 2, and
q is 0, if M is Ir;

or
X is a π-allyl group,
D is a non-coordinating anion such as e.g. $BF_4$, $ClO_4$, $PF_6$, $SbF_6$, $CF_3SO_3$, $BPh_4$, or BARF,
m, n, p and r are each 1, and
q is 0, if M is Pd.

Ph stands for a phenyl group, cod stands for (Z,Z)-1,5-cyclooctadiene, nbd stands for norbornadiene, and BARF stands for tetrakis[3,5-bis(trifluoromethyl)phenyl]borate. π-Methallyl and π-allyl stand for anionic ligands of the structures $H_2C{=}C(Me)\text{-}CH_2$ and $H_2C{=}CH\text{—}CH_2$.

Preferred transition metal complexes and methods for making such complexes are described below.

A ruthenium complex can be prepared, for example, by reaction of the Ru precursors $[Ru(cod)(OCOCF_3)_2]_2$, $[Ru(cod)(OCOCF_3)_2]_2H_2O$, $[Ru(cod)(OCOCH_3)_2]$ or $[Ru_2(cod)_2Cl_4(CH_3CN)]$ and the ligand of formula I in an inert solvent for example in ethers such as tetrahydrofuran or diethyl ether or mixtures thereof, or in dichloromethane as described in the literature (B. Heiser, E. A. Broger, Y. Crameri, Tetrahedron: Asymmetry 1991, 2, 51).

Another method for preparing a ruthenium complex comprises, for example, the reaction of the ruthenium precursor $[Ru(cod)(methallyl)_2]$ with a ligand of the formula I in a nonpolar solvent such as e.g. hexane or toluene or mixtures thereof as described in J. P. Genet, S. Mallart, C. Pinel, S. Juge, J. A. Laffitte, Tetrahedron: Asymmetry, 1991, 2, 43.

In situ preparation of ruthenium complexes can be performed for example by reaction of the ruthenium precursor $[Ru(cod)(methallyl)_2]$ with a ligand of the formula I in the presence of trifluoroacetic acid in methanol as described in the literature (B. Heiser, E. A. Broger, Y. Crameri, Tetrahedron: Asymmetry 1991, 2, 51).

A ruthenium complex can also be prepared, for example, by heating [Ru(cod)Cl$_2$]n and the ligand of formula I at reflux by use of toluene as a solvent in the presence of triethylamine as described in the literature (T. Ikariya, Y. Ishii, H. Kawano, T. Arai, M. Saburi, and S. Akutagawa, J. Chem. Soc., Chem. Commun. 1985, 922). Further a ruthenium complex can be prepared, for example, by heating [Ru(p-cymene)I$_2$]$_2$ and the ligand of formula I with stirring in a methylene chloride/ethanol mixture in accordance with the method described in the literature (K. Mashima, K. Kusano, T. Ohta, R. Noyori, H. Takaya, J. Chem. Soc., Chem. Commun. 1989, 1208)

Preferred ruthenium complexes are
Ru(OAc)$_2$(L), [Ru(OCOCF$_3$)$_2$(L)]$_2$, Ru$_2$Cl$_4$(L)$_2$NEt$_3$, [RuCl(benzene)(L)]Cl,
[RuBr(benzene)(L)]Br, [RuI(benzene)(L)]I, [RuCl(p-cymene)(L)]Cl, [RuBr(p-cymene)(L)]Br, [RuI(p-cymene)(L)]I, [Ru(L)](BF$_4$)$_2$, [Ru(L)](ClO$_4$)$_2$, [Ru(L)](PF$_6$)$_2$[Ru(L)](BPh$_4$)$_2$.

A rhodium complex can be prepared, for example, by reaction of rhodium precursors such as [Rh(cod)Cl]$_2$, [Rh(nbd)Cl]$_2$, [Rh(cod)$_2$]SbF$_6$, [Rh(cod)$_2$]BF$_4$, [Rh(cod)$_2$]ClO$_4$ with the ligand of formula I in accordance with the method described in "Experimental Chemistry, 4th edition" Vol. 18, Organometallic Complexes, pp. 339-344, Ed. Chemical Society of Japan, 1991, Maruzen.

Preferred rhodium complexes are
Rh(L)Cl, Rh(L)Br, Rh(L)I, [Rh(cod)(L)]SbF$_6$, [Rh(cod)(L)]BF$_4$, [Rh(cod)(L)]ClO$_4$,
[Rh(cod)(L)]PF$_6$, [Rh(cod)(L)]BPh$_4$, [Rh(cod)(L)]BARF, [Rh(nbd)(L)]SbF$_6$, [Rh(nbd)(L)]BF$_4$,
[Rh(nbd)(L)]ClO$_4$,
[Rh(nbd)(L)]PF$_6$, [Rh(nbd)(L)]BPh$_4$.

An iridium complex can be prepared, for example, by reacting the ligand of formula I with [Ir(cod)(CH$_3$CN)$_2$]BF$_4$ or with [Ir(cod)Cl]$_2$ in accordance with the method described in the literature (K. Mashima, T. Akutagawa, X. Zhang, H. Takaya, T. Taketomi, H. Kumobayashi, S. Akutagawa, J. Organomet., Chem. 1992, 428, 213).

Preferred iridium complexes are
Ir(L)Cl, Ir(L)Br, Ir(L)I, [Ir(cod)(L)]BF$_4$, [Ir(cod)(L)]ClO$_4$, [Ir(cod)(L)]PF$_6$, [Ir(cod)(L)]BPh$_4$, [Ir(nbd)(L)]BF$_4$, [Ir(nbd)(L)]ClO$_4$,
[Ir(nbd)(L)]PF$_6$, [Ir(nbd)(L)]BPh$_4$ A palladium complex can be prepared, for example, by reaction of the ligand of formula I with π-allylpalladium chloride in accordance with the method described in a literature (Y. Uozumi and T. Hayashi, J. Am., Chem. Soc. 1991, 113, 9887).

Preferred palladium complexes are
PdCl$_2$(L), [Pd(π-allyl)(L)]BF$_4$, [(Pd(π-allyl)(L)]ClO$_4$, [(Pd(π-allyl)(L)]PF$_6$, [(Pd(π-allyl)(L)]BPh$_4$ A nickel complex can be prepared, for example, by dissolving the ligand of formula I and nickel chloride in an alcohol such as isopropanol or ethanol or mixtures thereof and heating the solution with stirring in accordance with the method described in "Experimental Chemistry, 4th edition" Vol. 18, Organometallic Complexes, pp. 376, Ed. Chemical Society of Japan, 1991, Maruzen.

Preferred examples of nickel complexes are NiCl$_2$(L), NiBr$_2$(L) and NiI$_2$(L).

The transition metal complexes prepared as described above can be used as catalysts for asymmetric reactions, in particular for asymmetric hydrogenation reactions.

The following examples serve to illustrate the invention and do not in any manner represent a limitation.

All experiments were carried out under an atmosphere of deoxygenated argon. Solvents were dried and distilled under argon before use. The metal diphosphine complexes were prepared using Schlenk techniques.

EXAMPLE 1

Preparation of
rac-trans-4-hydroxy-1-phenyl-2-phospholene
1-oxide

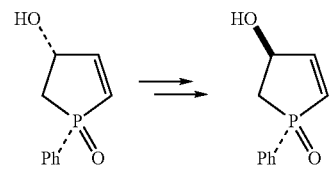

DIAD (6.2 mL, 30.9 mmol) was added dropwise at 0° C. to a stirred solution of TPP (7.87 g, 30.9 mmol), 3,5-dinitrobenzoic acid (6.36 g, 30.9 mmol) and cis-4-hydroxy-1-phenyl-2-phospholene 1-oxide (3.96 g, 20.4 mmol) in diethyl ether (300 mL). The resulting mixture was stirred 1 h at 0° C. and allowed to warm up and stirred at rt for two days. After that time the white sediment was filtered and washed with diethyl ether. The washed sediment was dissolved in methanol and 0.3 g of K$_2$CO$_3$ was added into obtained suspension. The reaction mixture was stirred at room temperature until hydrolysis was complete. The solvent was evaporated and the crude product was purified by column chromatography (hexane:ethyl acetate:methanol 5:3:1). Total yield 3.31 g (84%), of rac-trans-4-hydroxy-1-phenyl-2-phospholene 1-oxide, white crystals, mp=115-116° C. (ethyl acetate/hexane): $^1$H NMR (500 MHz), δ: 2.23-2.34 (ddd, J=4.5, J=15.8, J=20.3, 1H), 2.74-2.83 (ddd, J=4.1, J=7.7, J=15.8, 1H), 4.85-4.95 (m, 1H), 5.6 (d, J=9.4, 1H), 6.29-6.40 (ddd, J=1.6, J=8.2, J=22.0, 1H), 7.11-7.25 (ddd, J=2.2, J=8.2, J=37.2, 1H), 7.4-7.6 (m, 5H); $^{13}$C NMR (126 MHz), δ: 37.25 (d, J=66.9), 71.8 (d, J=16.8), 126.7 (d, J=89.0), 128.8 (d, J=12.4), 130.2 (d, J=10.8), 131.8 (d, J=100), 132.1 (d, J=2.8), 155.6 (d, J=18.5); $^{31}$P NMR (202 MHz), δ: 55.4; MS HR (EI): calcd for C$_{10}$H$_{11}$O$_2$P: 194.04967 found, 194.05024; Elemental anal. Calcd for C$_{10}$H$_{11}$O$_2$P: C. 61.91, H, 5.71, found C, 62.09, H, 5.65.

EXAMPLE 2

Synthesis of rac-trans-2-ethoxycarbonylmethyl-1-phenyl-3-phospholene 1-oxide

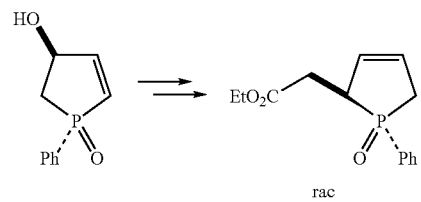

rac-trans-4-Hydroxy-1-phenyl-2-phospholene 1-oxide (3.8 g, 19.6 mmol) was refluxed in toluene with triethyl orthoacetate (40 mL, 222 mmol) and propionic acid (0.26 mL). After five days the solution was evaporated and the residue was purified by flash chromatography (hexane:ethyl acetate:methanol 5:3:0.5). Yield 4.43 g (85%), of rac-trans-2-ethoxycarbonylmethyl-1-phenyl-3-phospholene 1-oxide, yellow oil: $^1$H NMR (500 MHz), δ: 1.2 (t, J=7.1, 3H), 2.55-2.65 (ddd, J=17.2, J=13.7, J=8.2, 1H), 2.7-2.9 (m, 2H), 2.90-3.0 (ddd, J=17.2, J=9.6, J=7.1, 1H), 3.1-3.2 (m, 1H), 4.0-4.2 (m, 2H), 5.95-6.1 (m, 2H), 7.4-7.8 (m, 5H); $^{13}$C NMR (126 MHz), δ: 14.1, 33.1, 33.85 (d, J=66.6), 39.5 (d, J=68.5), 60.8, 127.25 (d, J=10.2), 128.65 (d, J=11.7), 129.75 (d, J=9.6), 131.95 (d, 2.9), 132.65 (d, J=13.8), 133.5 (d, J=92.8), 171.78 (d, J=10.2); $^{31}$P NMR (202 MHz), δ: 55.25. MS HR (ES): m/z=calcd 287.0808 (M+Na$^+$, C$_{14}$H$_{17}$O$_3$NaP), found 287.0812 (M+Na$^+$, C$_{14}$H$_{17}$O$_3$NaP).

EXAMPLE 2a

Enzymatic resolution of rac-trans-2-ethoxycarbonyl-methyl-1-phenyl-3-phospholene 1-oxide

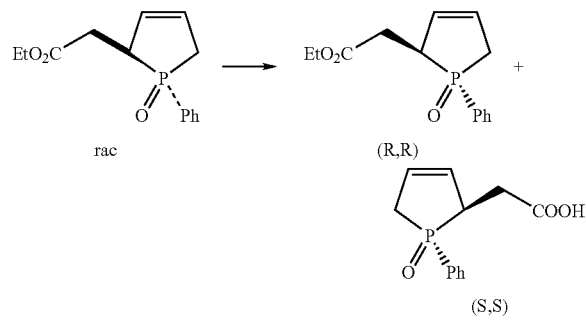

21.00 g (77.88 mmol) of rac-trans-2-ethoxycarbonylmethyl-1-phenyl-3-phospholene 1-oxide (98%) was emulsified in 6.75 L 0.1 M sodium chloride, 4 mM sodium phosphate pH 7.0 by vigorous stirring. 260 mg of ThermoCat Esterase E020 (ThermoGen; Chicago, USA) was added and the pH kept constant by the controlled addition (pH-stat) of 1.0 M sodium hydroxide solution under vigorous stirring. After nearly 50% conversion (21 h) the reaction mixture was extracted with 3×8 L dichloromethane and the combined organic phases dried (sodium sulfate) and evaporated to give the retained ester in 97% ee. The aqueous phase was acidified to pH 1.9 (conc. hydrochloric acid) and extracted with 4×6 L ethyl acetate. The combined organic phases were dried (sodium sulfate), evaporated and the residue dried on HV to give 8.85 g (48.1%) of (S,S)-trans-2-ethoxycarbonylmethyl-1-phenyl-3-phospholene 1-oxide as white solid: Analytics: MS: 235.1 (M–H); 99.4% (HPLC; 226 nm); 99.7% ee (methylated; GC on BGB-172; 30 m×0.25 mm; H$_2$ 150 kPa; 130-240° C. with 2° C./min; inj. 220° C.; det. 240° C.).

The retained (R,R)-ester was submitted to further hydrolysis in analogy to the procedure above until >99.5% ee were attained. After drying on HV 10.62 g (51.6%) of ethyl (R,R)-trans-2-ethoxycarbonylmethyl-1-phenyl-3-phospholene 1-oxide was obtained as a yellow-brownish oil: Analytics: EI-MS: 265.1 (48%), 264.1 (88%), 235.1 (36%), 219.1 (100%); 97.5% (HPLC; 226 nm); >99.8% ee (see above). The absolute configuration of the (S,S)-acid was established by X-ray determination.

EXAMPLE 3

Hydrogenation of (R,R)-trans-2-ethoxycarbonylmethyl-1-phenyl-3-phospholene 1-oxide

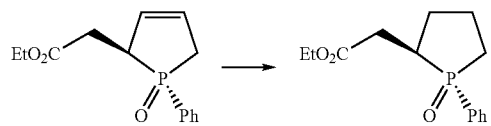

4.5 g of (R,R)-trans-2-ethoxycarbonylmethyl-1-phenyl-3-phospholene 1-oxide (17 mmol) was dissolved in 100 mL of methanol and the mixture was poured into Parr bottle. Argon was passed through the bottle for 10 minutes, and 0.15 g of Pd/C was carefully added. The bottle was installed in the Parr apparatus and hydrogen pressure of 4 atm. was applied followed by shaking of the reaction mixture overnight. After that the mixture was filtered through Celite, concentrated and the residue was purified by flash chromatography (hexane:ethyl acetate:methanol 5:3:1). Total yield 4.28 g (95%), of (R,R)-trans-2-ethoxycarbonylmethyl-1-phenylphospholane 1-oxide, yellow oil: $^1$H NMR (500 MHz), δ: 1.1 (t, J=7.1, 3H), 1.7-1.85 (m, 2H), 1.95-2.15 (m, 1H), 2.15-2.4 (m, 4H), 2.49-2.59 (ddd, J=8.3, 13.1, 17.0, 1H), 2.78-2.86 (ddd, J=6.4, J=8.8, J=17.0, 1H), 3.95-4.1 (m, 2H), 7.44-7.54 (m, 3H), 7.68-7.75 (m, 2H); $^{13}$C NMR (126 MHz), δ: 14.0, 23.3 (d, J=6.0), 30.0 (d, J=67.0), 31.6 (d, J=10.1), 32.5 (d, J=1.2), 36.2 (d, J=69.1), 60.6, 128.6 (d, J=11.7), 129.9 (d, J=9.6), 131.7 (d, J=2.9), 133.6 (d, J=90.3), 172.1 (d, J=11.1); $^{31}$P NMR (202 MHz), δ: 57.27; MS HR (ES): m/z=calcd 289.0964 (M+Na$^+$, C$_{14}$H$_{19}$O$_3$NaP), found 289.0980 (M+Na$^+$, C$_{14}$H$_{19}$O$_3$NaP); [α]$_D$=+18.75 (c 1.10, CHCl$_3$).

EXAMPLE 4

Preparation of (R,R)-trans-2-(2-hydroxyethyl)-1-phenylphospholane 1-oxide

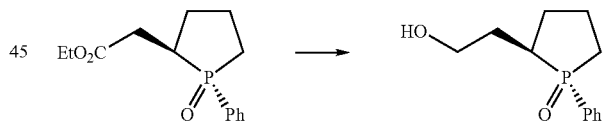

Methanol (14 mL) was added over a period of 1 h to the refluxing mixture of (R,R)-trans-2-ethoxycarbonylmethyl-1-phenylphospholane 1-oxide (4.8 g, 18.1 mmol) and NaBH$_4$ (1.41 g, 36.2 mmol) in THF (10 mL). After the addition of MeOH the reaction mixture was refluxed for one hour. After this time the solvent was evaporated and the residue was purified by flash chromatography (hexane:ethyl acetate: methanol 5:3:1). Total yield 3.97 g (98%), of (R,R)-trans-2-(2-hydroxyethyl)-1-phenylphospholane 1-oxide, white crystals, mp=126-126.5° C. (ethyl acetate/hexane/methanol): $^1$H NMR (500 MHz), δ: 1.72-1.97 (m, 3H), 2.01-2.33 (m, 6H), 3.31-3.36 (dd, J=5.35, J=5.70, 1H), 3.54-3.36 (m, 1H), 3.68-3.77 (m, 1H), 7.48-7.52 (m, 3H), 7.71-7.76 (m, 2H); $^{13}$C NMR (126 MHz), δ: 23.35 (d, J=6.1), 29.7 (d, J=66.85), 31.15 (d, J=2.6), 31.6 (d, J=10.7), 38.7 (d, J=67.7), 60.55 (d, J=4.9), 128.5 (d, J=11.5), 129.8 (d, J=9.5), 131.6 (d, J=2.9), 133.7 (d, J=88.85); $^{31}$P NMR (202 MHz), δ: 60.8; MS HR (LSIMS(+)): m/z=calcd 225.10444 (M+H$^+$, C$_{12}$H$_{18}$O$_2$P),

EXAMPLE 5

Preparation of (R,R)-trans-2-(2-methylsulfonyloxyethyl)-1-phenylphospholane 1-oxide

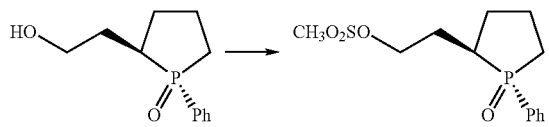

1.52 g (6.79 mmol) of (R,R)-trans-2-(2-hydroxyethyl)-1-phenylphospholane 1-oxide was dissolved in 50 mL of dry $CH_2Cl_2$ and cooled to 0° C. Next 10.6 mL of N-ethyldiisopropylamine and 1.78 g (10.2 mmol) of methanesulfonic anhydride were added. The reaction mixture was stirred 1 h at 0° C. and allowed to warm up and stirred at rt overnight. The solvent was evaporated and the residue was purified by flash chromatography (isopropanol:hexane 1:1). Total yield 1.91 g (93%), of (R,R)-trans-2-(2-methylsulfonyloxyethyl)-1-phenylphospholane 1-oxide, yellow oil: $^1H$ NMR (500 MHz), δ: 1.69-1.94 (m, 2H), 2.0-2.17 (m, 3H), 2.2-2.36 (m, 4H), 2.7 (s, 3H), 4.17-4.24 (ddd, J=5.1, J=7.5, J=10.1, 1H), 4.26-4.33 (dt, J=5.7, J=10.1, 2H), 7.45-7.57 (m, 3H), 7.69-7.77 (m, 2H); $^{13}C$ NMR (126 MHz), δ: 23.6 (d, J=5.65), 27.7, 30.2 (d, J=66.7), 31.6 (d, J=10.0), 36.8, 68.7 (d, J=7.15), 128.9 (d, J=11.5), 129.9 (d, J=9.6), 132.0 (d, J=2.6); $^{31}P$ NMR (202 MHz), δ: 57.62; MS HR (ES): m/z=calcd 325.0634 (M+Na$^+$, $C_{13}H_{19}O_4NaPS$), found 325.0650 (M+Na$^+$, $C_{13}H_{19}O_4NaPS$); $[α]_D$=-5.28 (c 0.63, CHCl$_3$).

EXAMPLE 6

Preparation of (R,R)-trans-2-[(2-diphenylphosphinoborane)ethyl]-1-phenylphospholane 1-oxide

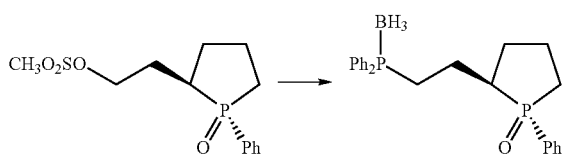

1.68 mL (9.76 mmol) of Ph$_2$PH was dissolved in 20 ml of dry THF, cooled to −78° C. and 7.3 mL (9.12 mmol) of n-BuLi was added. To the resulting deeply red mixture a solution of 2.12 g (7.0 mmol) of (R,R)-trans-2-(2-methylsulfonyloxyethyl)-1-phenylphospholane 1-oxide in 15 mL was added. The reaction mixture was stirred 1 h at −78° C., allowed to warm up and stirred at rt for 2 hours. After this time 14 mL of borane in THF (1M) was added and this mixture was stirred overnight. The solvent was evaporated and the residue was purified by flash chromatography (hexane:ethyl acetate:methanol 5:3:0.5). Yield 3.87 g (80%), of (R,R)-trans-2-[(2-diphenylphosphinoborane)ethyl]-1-phenylphospholane 1-oxide, colourless oil: $^1H$ NMR (500 MHz), δ: 0.5-1.4 (b, 3H), 1.63-1.81 (m, 2H), 1.86-2.26 (m, 8H), 2.51-2.63 (m, 1H), 7.13-7.19 (m, 1H), 7.22-7.59 (m, 10H), 7.66-7.79 (m, 4H); $^{13}C$ NMR (126 MHz), δ: 22. (d, J=2.1), 23.3 (d, J=6.0), 24.1 (dd, J=5.2, J=37.0), 30.3 (d, J=66.3), 31.7 (d, J=10.65), 41.45 (dd, J=12.1, J=68.0), 128.6-129.0 (m), 129.7 (d, J=55.5), 129.8 (d, 9.6), 129.8 (d, J=2.5), 131.2 (d, J=2.8), 131.9 (d, J=9.05), 132.4 (d, J=9.2), 134.3 (d, J=87.7); $^{31}P$ NMR (162 MHz), δ: 16.05 (b), 57.2; MS HR (ES): m/z=calcd 429.1679 (M+Na$^+$, $C_{24}H_{29}BONaP_2$), found 429.1679 (M+Na$^+$, $C_{24}H_{29}BONaP_2$); $[α]_D$=+64.99 (c 1.075, CHCl$_3$).

EXAMPLE 7

Synthesis of (S$_P$,R)-trans-2-(2-diphenylphosphinoethyl)-1-phenylphospholane P,P-diborane

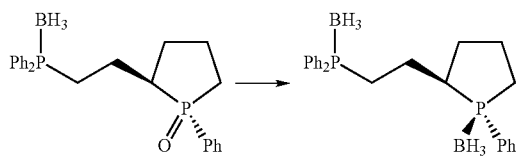

2.17 g (5.35 mmol) of (R,R)-trans-2-[(2-diphenylphosphinoborane)ethyl]-1-phenyl-phospholane 1-oxide was dissolved in 8 mL of toluene and 3.8 ml (26.7 mmol) of PhSiH$_3$ was added. The reaction mixture was heated at 45° C. for two days. Then 10 mL of borane in THF (1 M) was added and this mixture was stirred overnight. The solvent was evaporated and the residue was purified by flash chromatography (hexane:ethyl acetate 2:1). Total yield 1.62 g (75%), of (S$_P$,R)-trans-2-(2-diphenylphosphinoethyl)-1-phenylphospholane P,P-diborane, white crystals mp=114-114.5° C. (ethyl acetate/hexane): $^1H$ NMR (500 MHz), δ: 0.3-1.4 (bt, 6H, 2×BH$_3$), 1.51-1.63 (m, 1H), 1.78-2.30 (m, 8H), 2.35-2.47 (m, 1H), 2.55-2.67 (m, 1H), 7.33-7.38 (m, 2H), 7.40-7.57 (m, 9H), 7.69-7.78 (m, 4H); $^{13}C$ NMR (126 MHz), δ: 23.8 (d, J=5.5), 24.9 (dd, J=4.8, J=36.9), 26.0, 27.5 (d, J=39.1), 34.4 (d, J=6.9), 42.4 (dd, J=12.6, J=33.6), 128.7 (d, J=54.8), 128.7 (d, J=10.0), 128.8 (d, J=11.1), 129.0 (d, J=9.6), 129.9 (d, J=55.55), 131.0 (d, J=2.4), 131.3 (d, J=2.5), 131.4 (d, J=2.4), 131.6 (d, J=8.9), 131.8 (d, J=9.0), 132.7 (d, J=9.2); $^{31}P$ NMR (202 MHz), δ: 17.6 (b), 32.9 (b); MS HR (ES): m/z=calcd 427.2058 (M+Na$^+$, $C_{24}H_{32}B_2NaP_2$), found 427.2084 (M+Na$^+$, $C_{24}H_{32}B_2NaP_2$); Elemental anal. Calcd for $C_{24}H_{32}P_2B_2$ C, 71.35, H, 7.98, found C, 71.20, H, 7.28; $[α]_D$=+71.09 (c 0.73, CHCl$_3$).

EXAMPLE 8

Preparation of (S$_P$,R)-trans-2-(2-diphenylphosphino)ethyl-1-phenylphospholane{(S$_P$,R)-trans-PEP}

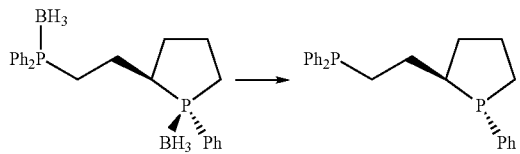

190 mg of (S$_P$,R)-trans-2-(2-diphenylphosphino)ethyl-1-phenylphospholane P,P-diborane was dissolved in 6 ml of benzene and 323 mg of DABCO was added. The mixture was stirred at rt overnight. The solvent was evaporated and the residue was purified by flash chromatography on Al$_2$O$_3$ (hexane/ethyl acetate 20:1) to afford 141 mg (80%), of (S$_P$,R)- trans-2-(2-diphenylphosphino)ethyl-1-phenylpholane, colourless oil: $^1$H NMR (500 MHz), δ: 1.0-1.1 (m, 1H), 1.42-1.9 (m, 8H), 2.11-2.21 (m, 1H), 2.23-2.33 (m, 1H), 2.37-2.47 (m, 1H), 7.0-7.12 (m, 9H), 7.32-7.39 (m, 2H), 7.46-7.55 (m, 4H); $^{13}$C NMR (126 MHz), δ: 26.65 (d, J=13.35), 27.9 (d, J=3.4), 28.7 (t, J=13.2), 31.8 (dd, J=17.15, J=29.8), 35.3, 46.2 (t, J=12.6), 127.6-128.4 (m), 128.5 (d, J=5.3), 128.6 (d, J=1.6), 128.7 (d, J=1.3), 128.72 (d, J=1.1), 131.1 (d, J=16.1), 133.1 (d, J=3.8), 133.2 (d, J=3.65), 139.5 (d, J=14.6), 139.9 (d, J=14.6), 142.9 (d, J=24.4); $^{31}$P NMR (162 MHz), δ: −16.16, −4.66; MS HR (ES): m/z=calcd 377.1583 (M+H$^+$, C$_{24}$H$_{27}$P$_2$), found 377.1565 (M+H$^+$, C$_{24}$H$_{27}$P$_2$).

EXAMPLE 9

Preparation of (R$_P$, S)-Cis-2-[(2-diphenylthiophosphinoyl)ethyl]-1-phenylphospholane 1-oxide

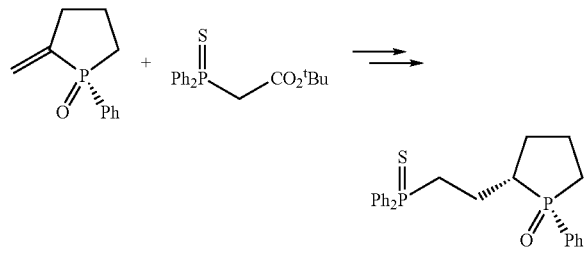

1 g (5.2 mmol) of (R)-2-methylene-1-phenylphospholane 1-oxide and 2 g (6.24 mmol) of (diphenylphosphinothioyl)acetic acid tert-butyl ester were dissolved in 16 mL of benzene. The mixture was cooled to 0° C. and 156 mg (7.72 mmol) of NaH was added. The mixture was stirred 30 minutes at 0° C. and allowed to warm up and stirred at rt for 24 hours. After that time the solvent was evaporated and the residue was purified by flash chromatography (hexane:ethyl acetate:methanol 5:3:1). The obtained mixture of diastereoisomers was dissolved in 20 mL of formic acid and stirred at rt overnight. Then the formic acid was evaporated and the residue was dissolved in 15 mL of pyridine and 104 mg of Cu$_2$O was added. The resulting mixture was refluxed for 12 hours. After that time the solution was evaporated and the residue was purified by flash chromatography (hexane:ethyl acetate:methanol 5:3:1). Total yield 0.96 g (42%), of (R$_P$,S)-cis-2-[(2-diphenylthiophosphinoyl)ethyl]-1-phenylphospholane 1-oxide, white crystals, mp=173-173.5° C. (ethyl acetate/hexane/methanol): $^1$H NMR (500 MHz), δ: 1.2-1.35 (m, 1H), 1.41-1.54 (m, 1H), 1.9-2.14 (m, 4H), 2.15-2.35 (m, 5H), 2.42-2.54 (m, 1H), 7.24-7.3 (m, 2H), 7.34-7.52 (m, 8H), 7.56-7.7.62 (m, 1H), 7.62-7.73 (m, 4H); $^{13}$C NMR (126 MHz), δ: 21.4, 22.1 (d, J=5.0), 28.4 (d, J=67.2), 30.9 (dd, J=4.3, J=56.15), 32.2 (d, J=13.1), 44.1 (dd, J=17.1, J=66.2), 128.2 (d, J=12.2), 128.3 (d, J=12.3), 128.4 (d, J=11.1), 130.3 (d, J=10.2), 130.5-130.6 (m), 130.7 (d, J=21.6), 130.9 (d, J=2.9), 131.1 (d, J=2.9), 131.35 (d, J=27.4), 131.7 (d, J=2.8), 132.75 (d, J=81.1); $^{31}$P NMR (202 MHz), δ: 42.4, 61.2; MS HR (ES): m/z=calcd 447.1072 (M+Na$^+$, C$_{24}$H$_{26}$ONaP$_2$S), found 447.1052 (M+Na$^+$, C$_{24}$H$_{26}$ONaP$_2$S); Elemental anal. Calcd for C$_{24}$H$_{24}$P$_2$OS: C, 67.99, H, 6.18, S, 7.55, found C, 67.87, H, 6.31, S, 7.85; [α]$_D$=+66.30 (c 0.745, CHCl$_3$).

EXAMPLE 10

Preparation of (R$_P$,S)-cis-2-(2-diphenylphosphinoethyl)-1-phenylphospholane P,P-disulfide

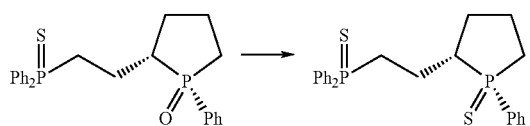

2.8 g (6.6 mmol) of (R$_P$,S)-cis-2-(2-diphenylphosphinoethyl)sulfido-1-phenylphospholane 1-oxide was dissolved in 8 mL of toluene and 5.0 mL (35.1 mmol) of PhSiH$_3$ was added. The reaction mixture was heated at 45° C. for two days. Then the solvent was evaporated and the residue was dissolved in 5 mL of benzene and 1 g of S$_8$ was added. This mixture was stirred at rt overnight. The solvent was evaporated and the residue was purified by flash chromatography (hexane:ethyl acetate 2:1). Yield 2.45 g (84%), of (R$_P$,S)-cis-2-(2-diphenylphosphinoethyl)-1-phenylphospholane P,P-disulfide, white crystals, mp=139-140° C. (ethyl acetate/hexane): $^1$H NMR (500 MHz), δ: 1.24-1.38 (m, 1H), 1.54-1.66 (m, 1H), 1.89-2.07 (m, 1H), 2.08-2.49 (m, 6H), 2.5-2.7 (m, 2H), 7.30-7.35 (m, 2H), 7.4-7.51 (m, 8H), 7.54-7.6 (m, 1H), 7.66-7.74 (m, 2H), 7.82-7.9 (m, 2H); $^{13}$C NMR (126 MHz), δ: 22.3, 23.7 (d, J=3.5), 30.95 (dd, J=4.2, J=55.9), 34.4 (d, J=10.1), 35.3 (d, J=54.1), 51.0 (dd, J=16.5, J=51.9), 128.5-128.7 (m), 130.1 (d, J=66.2), 130.8 (d, J=10.2), 130.9 (d, J=10.2), 131.2 (d, J=2.9), 131.4 (d, J=2.9), 131.8 (d, J=9.6), 131.9 (d, J=9.8), 133.2 (d, J=81.2); $^{31}$P NMR (162 MHz), δ: 43.7, 60.7; MS HR (ES): m/z=calcd 441.1024 (M+H$^+$, C$_{24}$H$_{27}$P$_2$S$_2$), found 441.1046 (M+H$^+$, C$_{24}$H$_{27}$P$_2$S$_2$); Elemental anal. Calcd for C$_{24}$H$_{26}$P$_2$S$_2$ C, 65.51, H, 5.95, S, 14.54, found C, 65.18, H, 5.77, S, 14.86; [α]$_D$=+46.50 (c 0.97, CHCl$_3$).

EXAMPLE 11

Preparation of (S$_P$,S)-cis-2-(2-diphenylphosphinoethyl)-1-phenylphospholane P,P-diborane

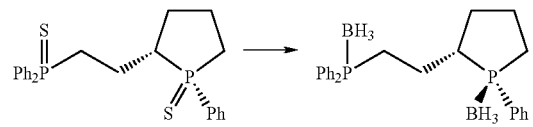

2.24 g (5.09 mmol) of (R$_P$,S)-cis-2-(2-diphenylphosphinoethyl)-1-phenylphospholane P,P-disulfide was dissolved in 35 mL of toluene and 7 mL (40.7 mmol) of Si$_2$Cl$_6$ was added. The reaction mixture was heated at 60° C. for 4 hours. After the time the solution was cooled to room temperature and 40 mL of 30% aqueous NaOH was slowly added to the reaction mixture in an ice-water bath. The resulting mixture was then stirred at rt until the aqueous layer became clear. The two phases were separated. The water phase was washed twice with toluene (2×30 mL). The combined toluene layers were dried over MgSO$_4$ and concentrated. The residue was redissolved in 10 mL of benzene and 15 mL of borane in THF (1 M) was added and this mixture was stirred overnight. The solvent was evaporated and the residue was purified by flash chromatography (hexane:ethyl acetate 2:1). Yield 1.98 g (88.8%), of (S$_P$,S)-cis-2-(2-diphenylphosphinoethyl)-1-phenylphospholane P,P-diborane, white crystals, mp=123-124° C. (ethyl acetate/hexane): $^1$H NMR (500 MHz), δ: 0.3-1.13 (bt, 6H, 2×BH$_3$), 1.15-1.29 (m, 1H), 1.49-1.6 (m, 1H), 1.63-1.86 (m, 2H), 2.01-2.32 (m, 7H), 7.22-7.29 (m, 4H), 7.34-7.45 (m, 6H), 7.46-7.54 (m, 3H), 7.63-7.68 (m, 2H); $^{13}$C NMR (126 MHz), δ: 23.3, 24.7 (dd, J=3.7, J=39.6), 24.9, 26.5 (d, J=37.1), 35.0, 42.7 (dd, J=14.9, J=34.6), 127.1 (d, J=43.0), 128.4 (d, J=61.9), 128.7 (d, J=8.3), 128.8 (d, J=8.4), 128.9 (d, J=9.6), 129.5 (d, J=55.6), 130.9 (d, J=2.3), 131.1 (d, J=2.3), 131.52 (d, J=2.9), 131.8 (d, J=9.2), 131.9 (d, J=9.3), 133.05 (d, J=8.7); $^{31}$P NMR (202 MHz), δ: 17.1 (b), 31.2 (b); MS HR (ES): m/z=calcd 427.2058 (M+Na$^+$, C$_{24}$H$_{32}$B$_2$NaP$_2$), found 427.2054 (M+Na$^+$, C$_{24}$H$_{32}$B$_2$NaP$_2$); Elemental anal. Calcd for C$_{24}$H$_{32}$P$_2$B$_2$ C, 71.35, H, 7.98, found C, 71.31, H, 8.32; [α]$_D$=+86.60 (c 0.885, CHCl$_3$).

EXAMPLE 12

Preparation of (S$_P$,S)-cis-2-(2-diphenylphosphino)ethyl-1-phenylphospholane{(S$_P$,S)-cis-PEP}

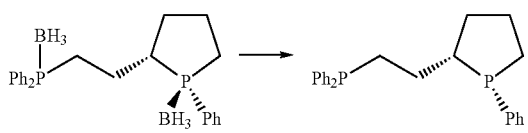

This ligand was prepared analogously as described for (S$_P$,R)-trans-2-(2-diphenylphosphino)ethyl-1-phenylphospholane in Example 8. Yield 96%, colourless oil: $^1$H NMR (300 MHz), δ: 1.00-1.70 (m, 5H), 1.80-2.15 (m, 5H), 2.20-2.35 (m, 1H), 6.95-7.25 (m, 10H), 7.35-7.50 (m, 5H); $^{13}$C NMR (75 MHz), δ: 22.71 (d, J=12.83), 24.92 (d, J=3.02), 25.81 (dd, J=2.26, J=18.11), 27.82 (dd, J=6.04, J=12.83), 32.02 (d, J=5.28), 43.46 (t, J=14.34), 126.70-127.50 (m), 131.62 (d, J=18.11), 131.89 (d, J=19.62), 132.75 (d, J=18.87), 136.03 (d, J=27.17), 138.12 (d, J=15.10), 138.65 (d, J=15.10); $^{31}$P NMR (121 MHz), δ: −15.86, −11.51.

EXAMPLE 13

Preparation of trans-2-[(2-hydroxy-methyl)ethyl]-1-phenylphospholane 1-borane

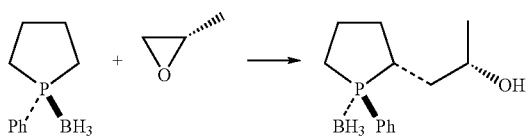

1 g (5.6 mmol) of 1-phenylphospholane 1-borane and 1.57 g (6.72 mmol) of (−)-sparteine were dissolved in 35 mL of dry Et$_2$O. This mixture was cooled to −78° C. and 6.1 mL (6.72 mmol) of sec-BuLi was added. This mixture was stirred 0.5 hour at −78° C. and then 5 mL of (S)-propylene oxide was added. The resulting yellow mixture was stirred 4.5 hours at −78° C. and allowed to warm up, whereafter the solvent was evaporated. The residue was dissolved in CH$_2$Cl$_2$, washed twice with 1 M HCl, dried over MgSO$_4$ and concentrated under vacuum. The residue was purified by flash chromatography (hexane:ethyl acetate 2:1).Yield 1 g (73%), of a mixture of two diastereoisomers (2:1), colourless oil: $^1$H NMR (300 MHz), δ: 0.1-1.0 (b, 3H, BH$_3$), 1.15 (d, J=6.0, 3H), 1.3-2.7 (m, 10H), 3.7-3.9 (m, 1H), 7.4-7.55 (m, 3H), 7.65-7.9 (m, 2H); $^{13}$C NMR (75 MHz), δ: 24.08, 24.14, 26.05, 26.13, 27.13 (d, I=39.2), 27.58 (d, J=40.0), 33.64 (d, J=7.5), 34.78 (d, J=7.5), 37.1, 37.5, 38.8-39.1 (m), 66.82 (d, J=9.1), 67.25 (d, J=5.3), 128.78 (d, J=9.8), 128.91 (d, J=9.8), 131.03, 131.11 (d, J=3.0), 131.32, 131.56 (d, J=9.0), 131.60 (d, J=9.0), 131.92; $^{31}$P NMR (121 MHz), δ: 31.7-33.8 (b); MS HR (ES): m/z=calcd 259.1395 (M+Na$^+$, C$_{13}$H$_{22}$BNaOP), found 259.1405 (M+Na$^+$, C$_{13}$H$_{22}$BNaOP).

EXAMPLE 14

Preparation of (S$_P$,R,S)-trans-2-[(2-methyl-methylsulfonyloxy)ethyl]-1-phenylphospholane 1-borane

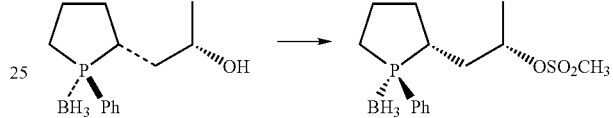

1.33 g (5.6 mmol) of trans-2-[(2-hydroxy-methyl)ethyl]-1-phenylphospholane 1-borane (two diastereomers) was dissolved in 37 mL of dry CH$_2$Cl$_2$ and cooled to 0° C. Then 8.5 mL of N-ethyldiisopropylamine and 1.46 g (8.4 mmol) of methanesulfonic anhydride were added. The reaction mixture was stirred 1 h at 0° C. allowed to warm up and stirred at rt overnight. The solvent was evaporated and the residue was purified by flash chromatography (hexane:ethyl acetate:methanol 5:3:1). The crystalline mixture of two diastereoisomers was recrystallized from ethyl acetate/hexane. The white crystals formed after standing overnight. $^1$H NMR monitoring showed that the resulting crystals contained a single diastereoisomer.

Yield 0.82 g (46%, de=100%), of (S$_P$,R,S)-trans-2-[(2-methyl-methylsulfonyloxy)ethyl]-1-phenylphospholane 1-borane, white crystals, mp=114-115° C. (ethyl acetate/hexane): $^1$H NMR (300 MHz), δ: 0.1-1.2 (b, 3H, BH$_3$), 1.36 (d, J=6.0, 3H), 1.4-1.7 (m, 1H), 1.8-2.3 (m, 6H), 2.4-2.6 (m, 2H), 2.97 (s, 3H), 4.8-5.0 (m, 1H), 7.4-7.6 (m, 3H), 7.7-7.9 (m, 2H); $^{13}$C NMR (75 MHz), δ: 21.45, 26.09, 26.87 (d, J=39.2), 33.26 (d, J=7.55), 36.26 (d, J=36.2), 36.56 (d, J=6.79), 38.86, 78.21 (d, J=12.1), 129.02 (d, J=9.81), 130.60 (d, J=45.3), 131.43 (d, J=3.02), 131.58 (d, J=9.06); $^{31}$P NMR (121 MHz), δ: 33.36-33.91 (b); [α]$_D$=+53.96 (c 1.03, CHCl$_3$).

EXAMPLE 15

Preparation of (S$_P$,R,R )-trans-2-(2-diphenylphosphino-2-methyl)ethyl-1-phenylphospholane P,P-diborane

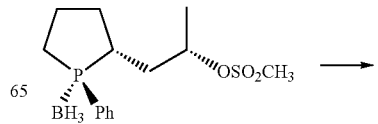

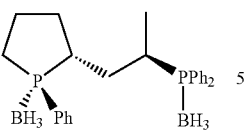

0.32 mL (1.91 mmol) of Ph₂PH was dissolved in 6 mL of THF, cooled to −78° C. and 212 mg (1.91 mmol) of t-BuOK was added. This mixture was stirred 10 min at this temperature. To the resulting orange mixture a solution of 0.5 g (1.59 mmol) of (S$_P$,R,S)-trans-2-[(2-methyl-methylsulfonyloxy)ethyl]-1-phenylphospholane 1-borane in 6 mL of THF was added. The reaction mixture was stirred 2 hours at −78° C. and allowed to warm up and stirred at rt 1 hour. After this time 3 mL of borane in THF (1M) was added and this mixture was stirred overnight. The solvent was evaporated and the residue was purified by flash chromatography (hexane:ethyl acetate 2:1). Yield 339 mg (51%, 100% de), of (S$_P$,R,R)-trans-2-(2-diphenylphosphino-2-methyl)ethyl-1-phenylphospholane P,P-diborane, white crystals, mp=175.5-176° C. (ethyl acetate/hexane): ¹H NMR (300 MHz), δ: 0.11-1.00 (b, 6H, 2×BH₃), 1.11-1.17 (dd, J=6.0, J=18.0, 3H), 1.25-1.60 (m, 2H), 1.65-2.25 (m, 7H), 2.40-2.60 (m, 1H), 7.25-7.75 (m, 15H); ¹³C NMR (75 MHz), δ: 25.87, 26.87 (d, J=38.5), 27.97 (d, J=9.81), 28.43 (d, J=8.30), 31.12 (dd, J=3.02, J=6.79), 33.38 (d, J=6.79), 38.83 (dd, J=7.55, J=33.97), 127.66, 128.00, 128.38, 128.69 (d, J=1.51), 128.82 (d, J=1.51), 128.96 (d, J=9.81), 130.94, 131.16-131.32 (m), 131.54, 131.71 (d, J=9.06), 132.72 (d, J=5.28), 132.84 (d, J=4.53); ³¹P NMR δ: (121 MHz), δ: 25.11-25.67 (b), 33.69-34.23 (b); MS (IS): m/z=436.2 (M+NH₄+, C₂₅H₃₈B₂NP₂); [α]$_D$=+103.3 (c 1.00, CHCl₃).

EXAMPLE 16

Preparation of (S$_P$,R,R)-trans-2-(2-diphenylphosphino-2-methyl)ethyl-1-phenylphospholane{(S$_P$,R,R)-trans-Me-PEP}

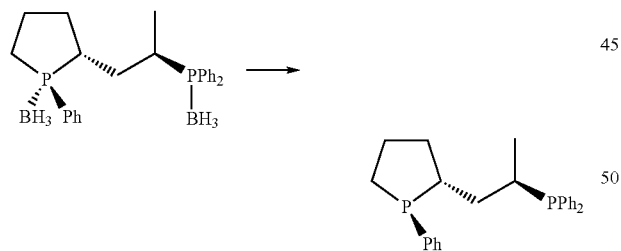

1.66 g of (S$_P$,R,R)-trans-2-(2-diphenylphosphino-2-methyl)ethyl-1-phenylphospholane P,P-diborane was dissolved in 70 mL of toluene and 3 g of DABCO was added. The mixture was stirred at rt for two days. The solvent was evaporated and the residue was purified by flash chromatography on Al₂O₃ (hexane:ethyl acetate 20:1), to afford 1.48 g (95.7%), of (S$_P$,R,R)-trans-2-(2-diphenylphosphino-2-methyl)ethyl-1-phenylphospholane, white solid: ¹H NMR (300 MHz), δ: 0.80-1.00 (m, 1H), 1.09 (dd, J=9.00, J=3H), 1.45-2.00 (m, 7H), 2.45-2.52 (m, 2H), 6.95-7.25 (m, 9H), 7.30-7.45 (m, 2H), 7.50-7.52 (m, 4H); ¹³C NMR (75 MHz), δ: 16.76 (d, J=14.34), 26.23 (d, J=14.34), 27.70 (d, J=3.02), 30.23 (dd, J=12.88, J=13.59), 39.48 (dd, J=18.87, J=32.46), 42.28 (dd, J=11.32, J=12.83), 128.45-128.75 (m), 128,89, 131.01 (d, J=16.61), 133.78 (d, J=18.87), 134.38 (d, J=19.62), 137.67 (d, J=17.36), 138.19 (d, J=16.61), 142.85 (d, J=25.66); ³¹P NMR δ: 12.50, 13.16.

EXAMPLE 17

Preparation of (S$_P$,R,R)-trans-2-[(2-methyl-methylsulfonyloxy)ethyl]-1-phenylphospholane 1-borane

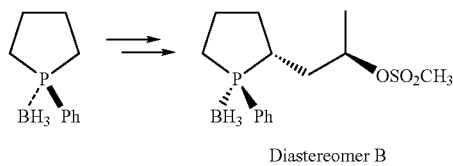

Diastereomer B

This compound was prepared analogously as described for (S$_P$,R,S)-trans-2-[(2-methyl-methylsulfonyloxy)ethyl]-1-phenylphospholane 1-borane in Example 13-14 but starting from (R)-propylene oxide. (S$_P$,R,R)-trans-2-[(2-methyl-methylsulfonyloxy)ethyl]-1-phenyl-pholane 1-borane (Diastereomer B) was obtained as a yellow oil (yield=80%, de=80%), after removing (R$_P$, S,R)-trans-2-[(2-methyl-methylsulfonyloxy)ethyl]-1-phenylphospholane 1-borane (Diastereomer A) by crystallization from ethyl acetate/hexane.

EXAMPLE 18

Preparation of (S$_P$,R,S)-trans-2-(2-diphenylphosphino-2-methyl)ethyl-1-phenylphospholane P,P-diborane

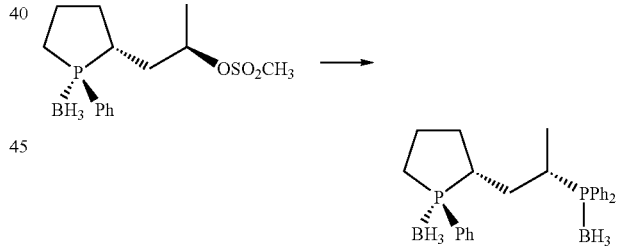

This compound was prepared analogously as described for the conversion of (S$_P$,R,R)-trans-2-[(2-methyl-methylsulfonyloxy)ethyl]-1-phenylphospholane 1-borane in Example 15. Yield 32% (de=100%), white crystals, mp=149-149.5° C.; ¹H NMR (300 MHz), δ: 0.15-1.40 (b, 6H, 2×BH₃), 0.70 (dd, J=6.00, J=18.01, 3H), 1.45-1.70 (m, 1H), 1.70-2.30 (m, 7H), 2.35-2.60 (m, 1H), 2.90-3.15 (m, 1H), 7.30-7.55 (m, 8H), 7.70-7.85 (m, 4H), 7.90-8.10 (m, 3H); ¹³C NMR (75 MHz), δ: 26.18, 26.78 (dd, J=3.77, J=36.23), 3.93 (dd, J=3.77, J=5.28), 35.43 (d, J=7.55), 39.06 (d, J=12.83), 39.51 (d, J=13.59), 127.81 (d, J=53.59), 128.62 (d, J=5.28), 128.75 (d, J=5.28), 129.06 (d, J=9.06), 129.31, 130.95-131.10 (m), 131.26 (d, J=2.26), 131.43 (d, J=131.57 (d, J=9.06), 132.43 (d, J=9.06), 133.28 (d, J=8.30); ³¹P NMR (121 MHz), δ: 24.87-25.41 (b), 28.99-29.42 (b); MS (IS): m/z=436.6 (M+NH₄+, C₂₅H₃₈B₂NP₂) [α]$_D$=+94.03 (c 0.982, CHCl₃).

EXAMPLE 19

Preparation of (S$_p$,R,S)-trans-2-(2-diphenylphosphino-2-methyl)ethyl-1-phenylphospholane{(S$_P$,R,S)-trans-Me-PEP

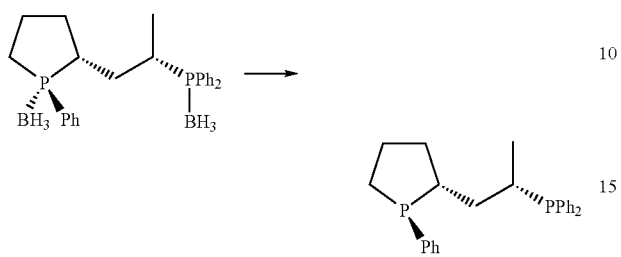

This compound was prepared analogously as described for the preparation of (S$_P$,R,R)-trans-2-(2-diphenylphosphino-2-methyl)ethyl-1-phenylphospholane in Example 16. Yield 98%, colourless oil: $^1$H NMR (300 MHz), δ: $^{13}$C NMR (75 MHz), δ: 15.99 (d, J=17.36), 26.26 (d, J=13.59), 27.53 (d, J=3.77), 30.16 (t, J=11.32), 38.92 (dd, J=18.11, J=25.66), 42.40 (d, J=11.32), 42.56 (d, J=12.08), 128.20-128.65 (m), 131.14 (d, J=16.60), 133.92 (d, J=3.02), 133.96 (d, J=19.62), 134.18 (d, J=2.26), 137.90 (d, J=15.10), 138.23 (d, J=15.85), 142.31 (d, J=24.15); $^{31}$P NMR (121 MHz), δ: −6.67, 0.02.

EXAMPLE 20

Epimerization of (S$_P$,R,R)-trans-2-(2-diphenylphosphino-2-methyl)ethyl-1-phenyl-phospholane

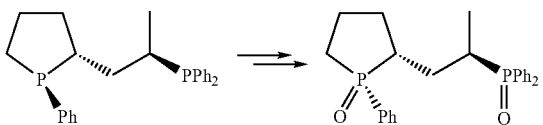

A solution of 150 mg of (S$_p$,R,R)-trans-2-(2-diphenylphosphino-2-methyl)ethyl-1-phenyl-phospholane in 7 mL of xylene was heated at 210° C. for 20 h (in a closed tube). Then the mixture was cooled to rt, 1 mL of H$_2$O$_2$ (15%) was added and obtained mixture was stirred at rt overnight. The organic phase was separated, dried over MgSO$_4$, the solvent was evaporated to afford a mixture of (S$_P$,R,R)-trans-Me-PEP dioxide ($^{31}$P NMR: δ37.74, 63.46; 85%), and (R$_P$,R,R)-cis-Me-PEP dioxide ($^{31}$P NMR: δ37.93, 63.46; 15%).

EXAMPLE 21

Epimerization of (S$_P$,R,S)-trans-2-(2-diphenylphosphino-2-methyl)ethyl-1-phenylphospholane{(S$_P$,R,S)-trans-Me-PEP}

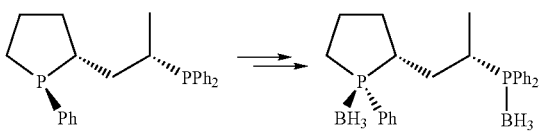

A solution of 140 mg of (S$_P$,R,S)-trans-2-(2-diphenylphosphino-2-methyl)ethyl-1-phenyl-phospholane in 7 mL of xylene was heated at 210° C. for 20 h (in a closed tube). Then the mixture was cooled to rt, 1 mL of BH$_3$-THF reagent (Aldrich) was added, and the obtained mixture was stirred at rt overnight. The solvent was evaporated and afforded a mixture of (S$_P$,R,S)-trans-Me-PEP bis(borane), ($^{31}$P NMR: δ29.05 (vbs), 25.2 (vbs), and (R$_P$,R,S)-cis-Me-PEP bis(borane), ($^{31}$P NMR: δ32.35 (vbs), 33.95 (vbs).

EXAMPLE 22

Preparation of rac-trans-2-(2-hydroxyethyl)-1-phenylphospholane 1-borane

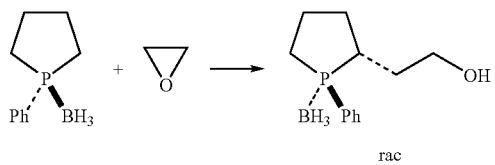

1 g (5.6 mmol) of 1-phenylphospholane 1-borane and 1.57 g (6.72 mmol) of (−)-sparteine were dissolved in 35 mL of dry Et$_2$O. The mixture was cooled to −78° C. and 6.1 mL (6.72 mmol) of sec-BuLi was added. This mixture was stirred 0.5 hour at −78° C. and then 5 mL of ethylene oxide was added. The resulting yellow mixture was stirred 4.5 hours at −78° C., allowed to warm up to room temperature, and evaporated. The residue was dissolved in CH$_2$Cl$_2$, washed twice with 1 M HCl, dried (MgSO$_4$), and concentrated under vacuum. The residue was purified by flash chromatography (hexane:ethyl acetate 2:1). Yield 0.56 g (45%), colourless oil: $^1$H NMR (200 MHz), δ: −0.1-1.2 (b, 3H, BH$_3$), 1.4-2.7 (m, 10H), 3.67 (t, J=6.2, 2H), 7.4-7.6 (m, 3H), 7.7-7.9 (m, 2H); $^{13}$C NMR (50 MHz), δ: 26.71, 27.79 (d, J=39.15), 33.02 (d, J=5.3), 34.54 (d, J=6.7), 37.7 (d, J=34.88), 62.19 (d, J=7.7), 129.4 (d, J=9.8), 131.69 (d, J=2.5), 132.08 (d, J=8.6); $^{31}$P NMR (121 MHz), δ: 32.9-33.9 (b).

EXAMPLE 23

Preparation of rac-trans-2-(2-hydroxyethyl)-1-phenylphospholane 1-oxide

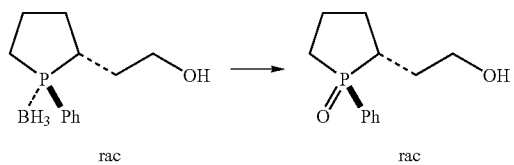

0.5 g (2.25 mmol) of 2-(2-hydroxyethyl)-1-phenylphospholane 1-borane was dissolved in 10 mL of toluene and 0.85 g of DABCO was added. The solvent was evaporated, the residue was dissolved in 30 mL of CH$_2$Cl$_2$ and 5 mL of H$_2$O$_2$ (15%) was added. This mixture was stirred at rt overnight, the organic phase was separated, dried over MgSO$_4$, and concentrated under vacuum. The residue was purified by flash chromatography (hexane:ethyl acetate:methanol 2:3: 1).Yield 0.45 g (90%), white crystals mp=126-126.5° C. (ethyl acetate/hexane/methanol): $^1$H NMR (500 MHz), δ: 1.72-1.97 (m, 3H), 2.01-2.33 (m, 6H), 3.31-3.36 (dd, J=5.35, J=5.7, 1H), 3.54-3.36 (m, 1H), 3.68-3.77 (m, 1H), 7.48-7.52 (m, 3H), 7.71-7.76 (m, 2H); $^{13}$C NMR (126 MHz), δ: 23.35 (d, J=6.1), 29.7 (d, J=66.85), 31.15 (d, J=2.6), 31.6 (d, J=10.7), 38.7 (d, J=67.7), 60.55 (d, J=4.9), 128.5 (d, J=11.5), 129.8 (d, J=9.5), 131.6 (d, J=2.9), 133.7 (d, J=88.85); $^{31}$P NMR (202 MHz), δ: 60.8; MS HR (LSIMS(+)): m/z=calcd 225.10444 (M+H$^+$, C$_{12}$H$_{18}$O$_2$P), found 225.10502 (M+H$^+$, C$_{12}$H$_{18}$O$_2$P); Elemental anal. Calcd for C$_{12}$H$_{17}$O$_2$P: C, 64.32, H, 7.65, found C, 63.93, H, 7.20.

EXAMPLE 24

Enzymatic resolution of rac-trans-2-(2-hydroxyethyl)-1-phenylphospholane 1-oxide

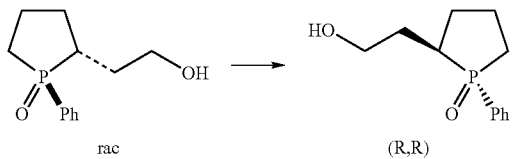

720 mg (3.21 mmol) of rac-trans-2-(2-hydroxyethyl)-1-phenylphospholane 1-oxide was dissolved in 650 ml TBME and 75 ml vinyl acetate and the solution cooled to 4° C. 720 mg of Lipase MAP-10 (Amano Enzyme Inc., Nagoya, Jpn.) was added under stirring and the suspension agitated gently at 4° C. After the enantiomeric excess of the retained alcohol had reached >98% (after 6 days) the enzyme was filtered off and the filtrate concentrated in vacuo. The residual oil was taken up in 7 ml acetonitrile/water 5:2 (white precipitate discarded) and chromatographed on Supelco ABZ$^+$(12 μm, 50×250 mm; gradient: 10% to 50% B in A within 25 min (A: 0.1% TFA in water; B: 0.1% TFA in acetonitrile); 100 ml/min; 270nm). The fractions containing the retained alcohol were pooled, evaporated and dried on HV to give 197 mg (27.4%) of (R,R)-2-(2-hydroxyethyl)-1-phenylphospholane 1-oxide as a white solid. Analytics: EI-MS: 225.3 (3.5%), 223.2 (10%), 194.2 (22%), 180.2 (100%); 96.6% (HPLC; 270 nm); 98.5% ee (HPLC on Chiralpak-ADH; 25 cm×4.6 mm; 90% heptane/10% EtOH; 0.8 ml/min; 25° C.; 220 nm); [α]$_D$=+23.10° (c=1.134 in CHCl$_3$). The absolute configuration was determined by chemical correlation.

EXAMPLE 25

Preparation of 2-[(2-hydroxy-phenyl)ethyl]-1-phenylphospholane 1-borane

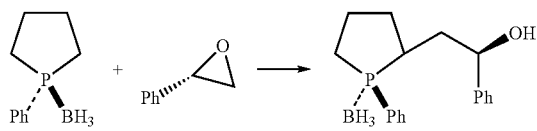

178 mg (1.0 mmol) of 1-phenylphospholane 1-borane and 0.28 g (1.2 mmol) of (−)-sparteine were dissolved in 8 mL of dry Et$_2$O. This mixture was cooled to −78° C. and 1.0 mL (1.2 mmol) of sec-BuLi was added. This mixture was stirred 0.5 hour at −78° C. and then 1 mL of (R)-styrene oxide was added. The resulting yellow mixture was stirred for 2 h at −78° C., allowed to warm up to room temperature, and stirred for an additional 2 h. The solvent was evaporated, the residue was dissolved in CH$_2$Cl$_2$, washed twice with 1 M HCl, dried (MgSO$_4$), and concentrated under vacuum. The residue was purified by flash chromatography (hexane:ethyl acetate 2:1) .Yield 0.11 g (37.5%), colourless oil: $^{31}$P NMR (121 MHz), δ: 31.9 (vbs); MS (ESI): m/z=316.5 (M+NH$_4^+$, C$_{18}$H$_{28}$BNOP).

EXAMPLE 25 A

Preparation of 1-phenylphospholane-1-sulfide

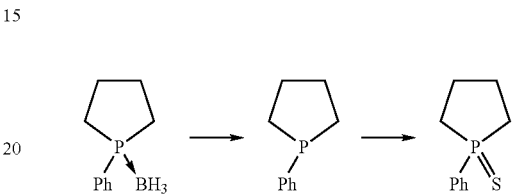

1 g (5.6 mmol) of 1-phenylphospholane 1-borane was dissolved in 25 mL of benzene and 2.2 g of DABCO was added. The mixture was stirred at rt overnight. The solvent was evaporated and the residue was dissolved in 40 mL toluene and 1.4 g of S$_8$ was added. This mixture was stirred overnight. The solvent was evaporated and the residue was purified by flash chromatography (hexane:ethyl acetate 2:1). Yield 1.065 g (97%), white crystals, mp=74° C. (methanol): $^1$H NMR (300 MHz), δ: 1.95-2.12 (m, 2H), 2.15-2.35 (m, 4H), 2.35-2.50 (m, 2H), 7.45-7.55 (m, 3H), 7.85-7.95 (m, 2H),$^{31}$P NMR (121 MHz), δ: 58.45. Elemental anal. Calcd for C$_{10}$H$_{13}$PS: C, 61.20, H. 6.68, found C. 61.25, H, 6.66.

EXAMPLE 25 B

Preparation of 2-[(2-hydroxy-2-phenyl)ethyl]-1-phenylphospholane-1-sulfide

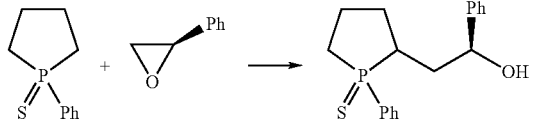

0.38 g (1.94 mmol) of 1-phenylphospholane 1-sulfide and 0.54 g (2.33 mmol) of (−)-sparteine were dissolved in 8 mL of dry THF. This mixture was cooled to −78° C. and 5.1 mL (7 mmol) of sec-BuLi was added. This mixture was stirred 0.5 hour at −78° C. and then 0.46 mL (3.88 mmol) of (R)-styrene oxide was added. The resulting brown mixture was stirred 2.5 hours at −78° C. and allowed to warm up, thereafter the solvent was evaporated. The residue was dissolved in CH$_2$Cl$_2$, washed twice with 1 M HCl, dried over MgSO$_4$ and concentrated under vacuum. The residue was purified by flash chromatography (hexane:ethyl acetate 2:1). Yield 0.315 g (51.5%) of a mixture of two diastereoisomers (1.25:1), as colourless oil and white crystals. Diastereoisomer A: white crystals, mp=141° C. (methanol); [α]$_D$=−30.5 (c 1.02, CHCl$_3$). $^1$H NMR (300 MHz), δ: 1.75-1.85 (m, 2H), 2.05-2.15 (m, 2H), 2.15-2.35 (m, 2H), 2.45-2.65 (m, 3H), 4.80-4.85 (dd, J=2.87, J=2.76, 1H), 7.10-7.30 (m, 5H), 7.45-7.60 (m, 3H), 7.90-8.00 (m, 2H), $^{13}$C NMR (75 MHz), δ:25.7, 25.73 (d, J=3.32), 33.98, 34.12 (d, J=10.78), 37.41, 38.13 (d, J=54.32), 39.09 (s), 39.53, 40.22 (d, J=51.83), 72.42, 72.46 (d, J=3.52), 125.72 (s), 127.52 (s), 128.61 (s), 128.92, 129.08 (d, J=11.40), 130.93, 131.06 (d, J=9.54), 131.79, 131.83 (d, J=3.11), 133.92, 134.85 (d, J=70.28), 144.67 (s), $^{31}$P NMR (121 MHz), δ: 61.46. Elemental anal. Calcd for $C_{18}H_{21}OPS$: C, 68.33, H, 6.69, found C, 68.63, H, 6.73; Diastereoisomer B: colourless oil; $[α]_D$=−29.7 (c 1.65, CHCl$_3$). $^1$H NMR (300 MHz), δ: 1.75-1.90 (m, 2H), 2.0-2.1 (m, 1H), 2.15-2.50 (m, 5H), 2.60-2.75 (m, 1H), 4.55-4.65 (dd, J=5.39, J=5.18, 1H), 7.05-7.15 (m, 2H), 7.20-7.30 (m, 3H), 7.50-7.60 (m, 3H), 7.85-7.95 (m, 2H), $^{13}$C NMR (75 MHz), δ: 25.63, 25.68 (d, J=3.52), 33.49, 33.63 (d, J=10.57), 37.08, 37.80 (d, J=54.52), 38.99 (s), 40.97, 41.66 (d, J=52.45), 73.60, 73.69 (d, J=6.84), 126.32 (s), 127.94 (s), 128.79 (s), 128.98, 129.143 (d, J=11.19), 130.98, 131.12 (d, J=9.74), 131.89, 131.93 (d, J=3.11), 133.63, 134.57 (d, J=71.52), 144.46 (s), $^{31}$P NMR (121 MHz), δ: 62.49.

EXAMPLE 25 C

Preparation of 2-{[2-diphenylphosphino(borane)-2-phenyl]ethyl}-1-phenylphospholane-1-sulfide (diastereomer A)

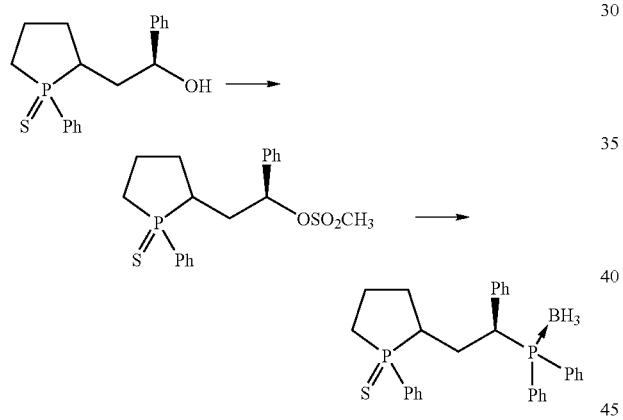

94 mg (0.297 mmol) of 2-[(2-hydroxy-2-phenyl)ethyl]-1-phenylphospholane-1-sulfide (diastereomer A) was dissolved in 5 mL of dry Et$_2$O and cooled to −20° C. Then, 0.34 mL of triethylamine and 0.028 mL (0.35 mmol) of methanesulfonic chloride were added. The reaction mixture was stirred 2 h at −20° C. The mixture was then cooled to −78° C., taken up without precipitate into a syringe, and was added to a Ph$_2$PLi solution prepared from 0.153 mL (0.89 mmol) of Ph$_2$PH and 0.73 mL (0.91 mmol) of n-BuLi in 4 mL of THF at −78° C. The resulting mixture was stirred 2 h at −78° C. and was then allowed to warm up and stirred at rt 1 hour. After this time 2 mL of borane in THF (1M) was added and this mixture was stirred overnight. The solvent was evaporated and the residue was purified by flash chromatography (hexane:ethyl acetate 2:1). Yield 19 mg (12.8%), of 2-{[2-diphenylphosphino(borane)-2-phenyl]ethyl}-1-phenylphospholane-1-sulfide, white crystals, mp=165° C. (methanol); $[α]_D$=+72.04 (c 0.825, CHCl$_3$). $^{31}$P NMR (121 MHz), δ: 24.55-26.05 (m), 58.15, 58.16 (d, J=1.85).

EXAMPLE 25 D

Preparation of 2-{[2-diphenylphosphino(borane)-2-phenyl]ethyl}-1-phenylphospholane-1-sulfide (diastereomer B)

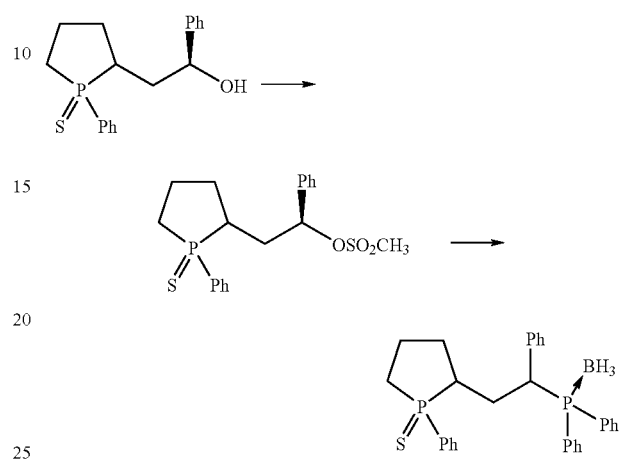

This compound was prepared analogously as described for the preparation of 2-{[2-diphenylphosphino(borane)-2-phenyl]ethyl}-1-phenylphospholane-1-sulfide (diastereomer A) but starting from 2-[(2-hydroxy-2-phenyl)ethyl]-1-phenylphospholane-1-sulfide (diastereomer B). Yield (4.5%), of 2-[(2-diphenylphosphinoborane-2-phenyl)ethyl]-1-phenylphospholane-1-sulfide, white crystals, mp=193° C. (methanol); $[α]_D$=+75.01 (c 0.765, CHCl$_3$). $^1$H NMR (300 MHz), δ: 1.55-1.80 (m, 2H), 1.90-2.05 (m, 1H), 2.05-2.30 (m, 4H), 2.45-2.60 (m, 2H), 3.71, 3.72, 3.75, 3.76, 3.77, 3.80, 3.81 (m, 1H), 7.0-7.80 (m, 20H), $^{31}$P NMR (121 MHz), δ: 24.45-26.00 (m), 61.91, 61.93 (d, J=1.86).

EXAMPLE 25 E

Preparation of 2-{[2-diphenylphosphino(borane)-2-phenyl)ethyl}-1-phenylphospholane-1-borane (diastereomer A)

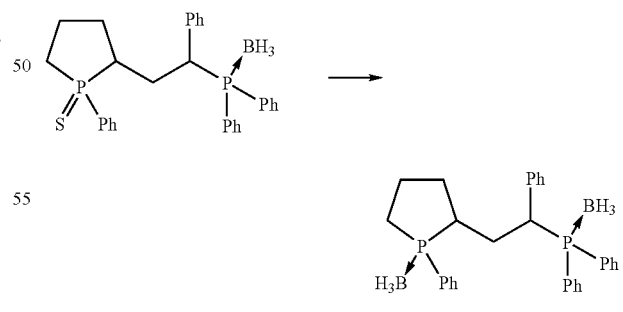

15 mg (0.03 mmol) of 2-{[2-diphenylphosphino(borane)-2-phenyl]ethyl}-1-phenylphospholane-1-sulfide (diasteroisomer A) was dissolved in 0.3 mL of benzene and 0.032 mL (0.18 mmol) of Si$_2$Cl$_6$ was added. The reaction mixture was heated at 60° C. for 1.5 h. The solution was cooled to rt and 5 mL of 30% aqueous NaOH was slowly added to the reaction mixture immersed in an ice-water bath. The resulting mixture was then stirred at rt until the aqueous layer became clear. The two phases were separated. The water phase was washed twice with toluene (2×30 mL). The combined toluene layers were dried over MgSO$_4$, filtered, and concentrated. The residue was redissolved in 4 mL of benzene and 0.2 mL of borane in THF (1 M) was added and this mixture was stirred overnight. The solvent was evaporated and the residue was purified by flash chromatography. Yield 10.8 mg, (75%). mp=169° C. (methanol); [α]$_D$=+110.5 (c 0.265, CHCl$_3$). $^{31}$P NMR (121 MHz), δ: 23.31-26.2 (m), 27.32-29-65 (m).

EXAMPLE 25 F

Preparation of 2-{[2-diphenylphosphino(borane)-2-phenyl)et]yl}-1-phenylphospholane-1-borane (diastereomer B)

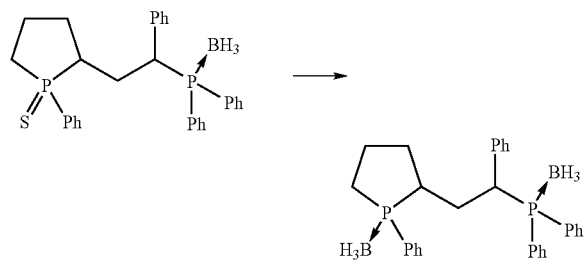

This compound was prepared analogously as described for the preparation of 2-{[2-diphenylphosphino(borane)-2-phenyl)ethyl}-1-phenylphospholane-1-borane (diastereomer A) but starting from 2-{[2-diphenylphosphino(borane)-2-phenyl]ethyl}-1-phenylphospholane-1-sulfide (diasteroisomer B). Yield: 82%. mp=189° C. (methanol); [α]$_D$=+58.67 (c 0.375, CHCl$_3$). $^{31}$P NMR (121 MHz), δ: 23.5-26.0 (m), 33.84-36.08 (m).

EXAMPLE 25 G

Preparation of 2-[(2-diphenylphosphino-2-phenyl)ethyl}-1-phenylphospholane (diastereomer A)

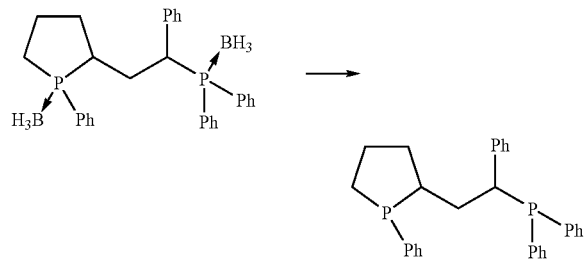

5.3 mg (0.012 mmol) of 2-{[2-diphenylphosphino(borane)-2-phenyl)ethyl}-1-phenylphospholane-1-borane (diasteroisomer A) was dissolved in 0.5 mL of toluene and 35 mg of DABCO was added. The mixture was stirred at rt for one day. Evaporation of the mixture gave the free diphosphine. Yield: 100%. $^{31}$P NMR (121 MHz), δ: 1.29, −6.49.

EXAMPLE 25 H

Preparation of 2-[(2-diphenylphosphino-2-phenyl)ethyl}-1-phenylphospholane (diastereomer B

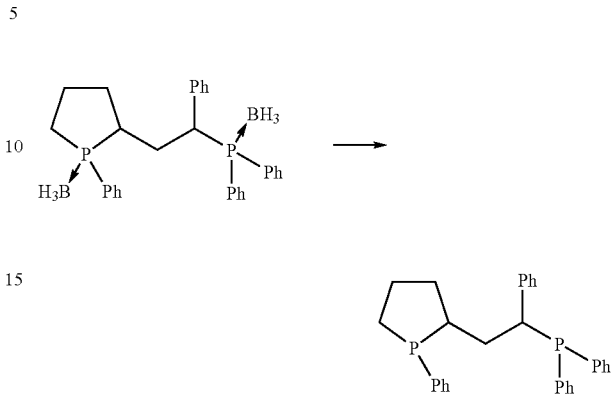

11 mg (0.022 mmol) of 2-{[2-diphenylphosphino(borane)-2-phenyl)ethyl}-1-phenylphospholane-1-borane (diastereoisomer B) was dissolved in 0.6 mL of toluene and 35 mg of DABCO was added. The mixture was stirred at rt for one day. Evaporation of the mixture gave the free diphosphine. Yield: 100%. $^{31}$P NMR (121 MHz), δ: 0.29 (d, J=1.88), 0.01 (d, J=1.88).

EXAMPLE 26

Preparation of [(η$^2$-1,2,5,6)-1,5-cyclooctadiene][(S$_P$,R)-trans-2-(2-diphenylphosphinoethyl-κP)-(1-phenylphospholane-κP)]rhodium(I)hexafluoroantimonate{[Rh(cod)((S$_P$,R )-trans- PEP)]]SbF$_6$}

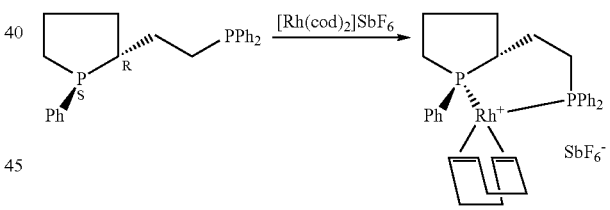

To a suspension of [Rh(cod)$_2$]SbF$_6$ (148.0 mg, 0.27 mmol) in THF (6 mL) in a 25 mL Schlenk tube, was added dropwise at −78° C. a solution of (S$_P$,R)-trans-2-(2-diphenyl-phosphino)ethyl-1-phenylphospholane (100.5 mg, 0.27 mmol) in THF (2 mL). The mixture was allowed to warm and stirred at room temperature during 2 h. After this time the solvent was evaporated. The yellow powder was washed twice with hexane and dried for 12 h in high vacuum affording 210 mg (94%) of [(η$^2$-1,2,5,6)-1,5-cyclooctadiene][(S$_P$,R)-trans-2-(diphenylphosphinoethyl-κP)-(1-phenylphospholane-κP)] rhodium(I)hexafluoroantimonate, yellow powder: $^1$H NMR (300 MHz), δ: 1.45-1.70 (m, 3H), 1.75-2.70 (m, 17H), 4.15-4.28 (b, 1H), 4.30-4.45 (b, 1H), 4.55-4.65 (b, 1H), 7.40-4.65 (m, 13H), 7.70-7.85 (m, 2H); $^{13}$C NMR (75 MHz), δ: 24.29, 24.55, 24.76, 24.89, 25.21 (d, J=10.57), 26.10-26.40 (m), 30.05, 30.36 (d, J=15.10), 33.19 (d, J=3.02), 39.85-40.00 (m), 40.27 (dd, J=1.51, J=4.53), 98.60-99.00 (m), 100.00-100.40 (m), 101.24 (d, J=6.79), 101.36 (d, J=7.55), 102.35-102.65

(m), 129.23 (d, J=9.81), 129.44 (d, J =6.04), 129.57 (d, J=6.79), 130.43, 130.55, 131.12, 131.69 (d, J=3.77), 131.92 (d, J=2.26), 132.25, 132.27 (d, J=9.81), 133.18 (d, J=35.47), 134.23 (d, J=12.08); $^{31}$P NMR (121 MHz), δ: 17.64 (dd, J=51.02, J=140.93), 24.76 (dd, J=52.24, J=137.28); ESI MS m/z: 822-235 (M-SbF$_6$)$^+$; Elemental anal. Calcd for C$_{32}$H$_{38}$P$_2$SbF$_6$Rh: C, 46.69, H, 4.65, F, 13.85, P, 7.52 found C, 46.84, H. 4.79, F, 13.43, P, 7.22

Preparation of [(η$^2$-1,2,5,6)-1,5-cyclooctadiene][(S$_P$,S)-cis-2-(diphenylphosphinoethyl-κP)-(1-phenylphospholane-κP)]rhodium(I)hexafluoroantimonate{[Rh(cod)((S$_P$,S)-cis-PEP)]SbF$_6$}

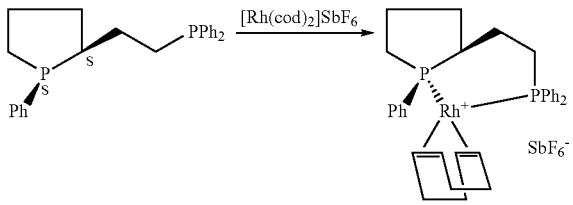

The [(η$^2$-1,2,5,6)-1,5-cyclooctadiene][(S$_P$,S)-cis-2-(diphenylphosphinoethyl-κP)-(1-phenylphospholane-κP)]rhodium(I)hexafluoroantimonate was prepared according to the procedure described in Example 26 a) starting from (S$_P$,S)-cis-2-(2-diphenylphosphino)ethyl-1-phenylphospholane. Yield 92%, yellow powder; $^1$H NMR (300 MHz), δ: 1.50-1.65 (m, 1H), 1.72-2.80 (m, 20H), 4.20-4.35 (b, 1H), 4.15-4.30 (b, 1H), 5.10-5.20 (b, 1H), 5.35-5.50 (b, 1H), 5.52-5.65 (b, 1H), 7.20-7.35 (m, 2H), 7.35-7.65 (m, 9H), 7.70-7.90 (m, 4H); $^{31}$P NMR (121 MHz), δ: 9.88 (dd, J=50.50, J=142.90), 23.13 (dd, J=50.30, J=140.90); ESI MS m/z: 822-235 (M-SbF$_6$)$^+$; Elemental anal. Calcd for C$_{32}$H$_{38}$P$_2$SbF$_6$Rh: C, 46.69, H, 4.65, F, 13.85, P, 7.52 found C. 47.18, H, 4.63, F, 13.20, P, 6.84.

Preparation of [(η$^2$-1,2,5,6)-1,5-cyclooctadiene][(S$_P$,R,R)-trans-2-(2-diphenylphosphino-2-methyl-ethyl-κP)-(1-phenylphospholane-κP)]rhodium(I)hexafluoroantimonate{[Rh(cod)- (S$_P$,R,R)(trans-Me-PEP)]SbF$_6$}

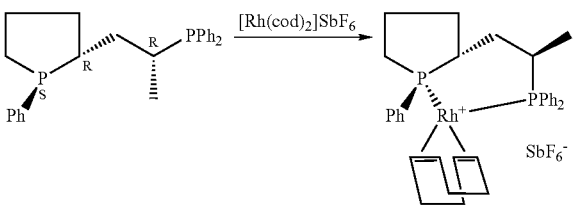

The [(η$^2$-1,2,5,6)-1,5-cyclooctadiene][(S$_P$,R,R)-trans-2-(2-diphenylphosphino-2-methyl -ethyl-κP)-(1-phenylphospholane-κP)]rhodium(I)hexafluoroantimonate was prepared according to the procedure described in Example 26 a) starting from (S$_P$,R,R)-trans-2-(2-diphenylphosphino-2-methyl)ethyl-1-phenylphospholane. Yield 94%, orange powder; $^1$H NMR (300 MHz), δ: 1.31 (dd, J=6.00, J=12.00, 3H), 1.50-2.2.90 (m, 18H), 4.10-4.45 (b, 2H), 4.95-5.15 (b, 1H), 5.00-5.20 (b, 1H), 7.40-7.65 (m, 11H), 7.70-7.85 (m, 2H), 7.90-8.00 (m, 2H); $^{31}$P NMR (121 MHz), δ: 22.76 (dd, J=49.81, J=134.85), 26.52 (dd, J=49.81, J=140.93); ESI MS (+) m/z: 601 (M-SbF$_6$)$^+$; ESI MS (−) m/z: 235 (SbF$_6$)$^-$.

Preparation of [(η$^2$-1,2,5,6)-1,5-cyclooctadiene][(S$_P$,R,S)-trans-2-(2-diphenylphosphino-2-methyl-ethyl-κP)-(1-phenylphospholane-κP)]rhodium(I)hexafluoroantimonate{[Rh(cod)((S$_P$,R,S)-trans-Me-PEP)]SbF$_6$}

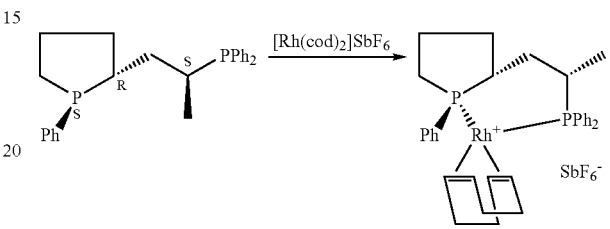

The [(η$^2$-1,2,5,6)-1,5-cyclooctadiene][(S$_P$,R,S)-trans-2-(2-diphenylphosphino-2-methyl-ethyl-κP)-(1-phenylphospholane-κP)]rhodium(I)hexafluoroantimonate was prepared according to the procedure described in Example 26 a) starting from (S$_P$,R,S)-trans-2-(2-diphenylphosphino-2-methyl)ethyl-1-phenylphospholane. Yield 94%, orange powder: $^1$H NMR (300 MHz), δ: 0.95 (dd, J=6.00, J=12.00, 3H), 1.15-1.45 (m, 2H), 1.50-2.85 (m, 20H), 4.05-4.20 (b, 1H), 4.45-4.55 (b, 1H), 4.60-4.75 (b, 1H), 5.25-5.45 (b, 1H), 7.30-7.45 (m, 2H), 7.50-7.60 (m, 6H), 7.60-7.75 (m, 3H), 7.85-7.95 (m,2H), 7.95-8.15 (m, 2H); $^{31}$P NMR (121 MHz), δ: 26.00 (dd, J=48.10, J=139.80), 32.25 (dd, J=48.30, J=139.81); ESI MS (+) m/z: 601 (M-SbF$_6$)$^+$.

Preparation of [(η$^2$-1,2,5,6)-1,5-cyclooctadiene][(S$_P$,R)-trans-2-(2-diphenylphosphinoethyl-κP)- (1-phenylphospholane-κP)]rhodium(I)tetrafluoroborate {[Rh(cod)((S$_P$, R)-trans-PEP)]BF$_4$}

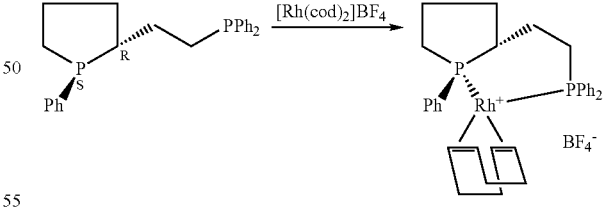

The [(η$^2$-1,2,5,6)-1,5-cyclooctadiene][(S$_P$,R)-trans-2-(2-diphenylphosphinoethyl-κP)-(1-phenylphospholane-κP)]rhodium(I)tetrafluoroborate was prepared according to the procedure described in Example 26 a) but with [Rh(cod)$_2$]BF$_4$ as a precursor. Yield 95%, yellow powder: $^1$H NMR (300 MHz), δ: 1.00-2.80 (m, 20H), 4.15-4.25 (b, 1H), 4.30-4.40 (b, 1H), 4.55-4.65 (b, 1H), 5.20-5.40 (b, 1H), 7.35-7.65 (m, 13H), 7.70-7.95 (m, 2H); $^{31}$P NMR (121 MHz), δ: 17.88 (dd, J=51.02, J=142.14), 24.69 (dd, J=51.02, J=136.07); ESI MS m/z: 674-87 (M-BF$_4$)$^+$.

Preparation of [(η²-1,2,5,6)-1,5-cyclooctadiene][($S_P$,S)-cis-2-(diphenylphosphinoethyl-κP)-(1-phenylphospholane-κP)]rhodium(I)tetrafluoroborate {[Rh(cod)(($S_P$,S)-cis-PEP)]BF4}

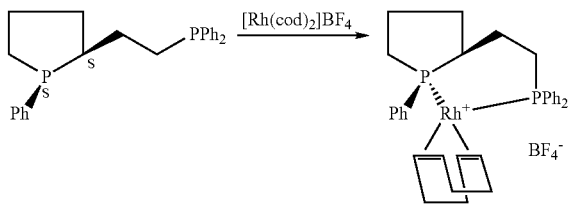

The [(η²-1,2,5,6)-1,5-cyclooctadiene][($S_P$,S)-cis-2-(diphenylphosphinoethyl-κP)-(1-phenylphospholane-κP)]rhodium(I)tetrafluoroborate was prepared according to the procedure described in Example 26 a) starting from ($S_P$,S)-cis-2-(2-diphenylphosphino)ethyl-1-phenylphospholane as a ligand and [Rh(cod)$_2$]BF$_4$ as a precursor. Yield 94%, orange powder: $^1$H NMR (300 MHz), δ: 1.40-2.80 (m, 20H), 4.20-4.40 (b, 1H), 4.60-4.80 (b, 1H), 5.05-5.20 (b, 1H), 5.40-5.55 (b, 1H), 7.30-7.65 (m, 11H), 7.70-7.95 (m, 4H); $^{31}$P NMR (121 MHz), δ: 10.06 (dd, J=52.24, J=144.57), 22.43 (dd, J=52.24, J=140.93); ESI MS m/z: 674-87 (M-BF$_4$)$^+$.

Preparation of [(η²-1,2,5,6)-1,5-cyclooctadiene][($S_P$,R)-trans-2-(2-diphenylphosphinoethyl-κP)-(1-phenylphospholane-κP)]rhodium(I)tetrakis[3,5-bis(trifluoromethyl)phenyl]borate {[Rh(cod)(($S_P$,R)-trans-PEP)]BARF}

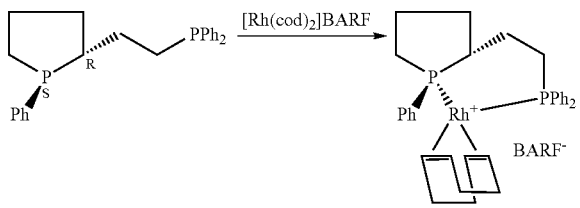

The [(η²-1,2,5,6)-1,5-cyclooctadiene][($S_P$,R)-trans-2-(2-diphenylphosphinoethyl-κP)-(1-phenylphospholane-κP)]rhodium(I)tetrakis[3,5-bis(trifluoromethyl)phenyl]borate was prepared according to the procedure described in Example 26 a) but with [Rh(cod)$_2$]BARF as a precursor and toluene as a solvent. Yield 95%, yellow powder: $^1$H NMR (300 MHz), δ: 1.30-1.65 (m, 3H), 1.70-2.65 (m, 16H), 4.20-4.35 (b, 1H), 4.40-4.50 (b, 1H), 4.55-4.65 (b, 1H), 5.10-5.30 (b, 1H), 7.05-7.32 (m, 4H), 7.35-7.65 (m, 14H), 7.70-7.95 (m, 9H); $^{31}$P NMR (121 MHz), δ: 17.15 (dd, J=51.02, J=140.93), 25.61 (dd, J=49.81, J=136.07); ESI MS (+) m/z: 587 (M-BARF)$^+$; ESI MS (−) m/z: 863 (BARF)$^-$.

EXAMPLES OF HYDROGENATIONS

The Hydrogenation Experiments were Carried as Follows:
In a glove box, an autoclave with a 20 mL glass tube insert equipped with a magnetic stirring bar was charged with the hydrogenation substrate (1 mmol), anhydrous degassed solvent (7 mL) and the metal complex pre-catalyst (0.01 mmol). After 10 cycles of evacuation and filling with hydrogen, the autoclave was pressurised to an appropriate initial pressure of hydrogen. The reaction mixture was stirred at room temperature and after the appropriate time the autoclave was opened, the reaction mixture was filtered through silica gel, concentrated and the residue was analysed by enantioselective GC.

EXAMPLE A

Hydrogenation of α-acetamidoacrylic acid and methyl α-acetamidoacrylate, respectively, using an isolated pre-catalyst [Rh(Ligand)(cod)]SbF$_6$ (with cis-PEP, trans-PEP, ($S_P$,R,R)-Me-PEP and ($S_P$,R,S)-Me-PEP as the Ligand).

TABLE A

| Substrate | Ligand | Solvent | % conv.# | % ee# (conf.)* |
|---|---|---|---|---|
| CO$_2$H / NHAc | (Sp, S)-cis-PEP | MeOH | 100 | 30 (S) |
| | (Sp, R)-trans-PEP | MeOH | 100 | <1 (S) |
| | (Sp, S)-cis-PEP | MeOH | 100 | 30 (S) |
| | (Sp, R)-trans-PEP | MeOH | 100 | <1 (S) |
| | (Sp, R, R)-Me-PEP | THF | 100 | 31 (S) |
| | (Sp, R, S)-Me-PEP | THF | 100 | 77 (R) |
| CO$_2$Me / NHAc | (Sp, S)-cis-PEP | MeOH | 100 | 23 (S) |
| | (Sp, R)-trans-PEP | MeOH | 100 | 8 (R) |
| | (Sp, S)-cis-PEP | THF | 100 | 15 (R) |
| | (Sp, R)-trans-PEP | THF | 100 | 13 (R) |
| | (Sp, R, R)-Me-PEP | MeOH | 100 | 11 (S) |
| | (Sp, R, R)-Me-PEP | THF | 100 | 12 (S) |
| | (Sp, R, S)-Me-PEP | THF | 100 | 67 (R) |

All reactions were performed at room temperature with a substrate concentration of 0.14M and 1 mol % of catalyst. Reactions were complete during 3 hours.
Determined by enantiodiscriminating GC.
*The absolute configuration was assigned by comparison of the sign of optical rotation with reported data.

All reactions were performed at room temperature with a substrate concentration of 0.14 M and 1 mol % of catalyst. Reactions were complete during 3 hours. #Determined by enantiodiscriminating GC. * The absolute configuration was assigned by comparison of the sign of optical rotation with reported data.

EXAMPLE B

Hydrogenation of α-acetamidocinnamic acid and methyl α-acetamidocinnamate, respectively, using an isolated pre-catalyst [Rh(Ligand)(cod)]SbF$_6$ (with cis-PEP, trans-PEP, ($S_P$,R,R)-Me-PEP and ($S_P$,R,S)-Me-PEP as the Ligands).

TABLE B

| Substrate | Ligand | Solvent | % conv.a | % ee# (conf.)* |
|---|---|---|---|---|
| Ph / CO$_2$H / NHAc | (Sp, S)-cis-PEP | MeOH | 100 | 24 (S) |
| | (Sp, R)-trans-PEP | MeOH | 100 | 34 (S) |
| | (Sp, R, R)-Me-PEP | THF | 100 | 53 (S) |
| | (Sp, R, S)-Me-PEP | THF | 100 | 39 (R) |
| Ph / CO$_2$Me / NHAc | (Sp, S)-cis-PEP | MeOH | 100 | 3 (R) |
| | (Sp, R)-trans-PEP | MeOH | 100 | 25 (S) |
| | (Sp, S)-cis-PEP | THF | 100 | 10 (R) |
| | (Sp, R)-trans-PEP | THF | 100 | 22 (S) |
| | (Sp, R, R)-Me-PEP | THF | 100 | 26 (S) |
| | (Sp, R, S)-Me-PEP | THF | 100 | 25 (R) |

All reactions were performed at room temperature with a substrate concentration of 0.14M and 1 mol % of catalyst. Reactions were complete during 3 hours.
Determined by enantiodiscriminating GC.
*The absolute configuration was assigned by comparison of the sign of optical rotation with reported data.

All reactions were performed at room temperature with a substrate concentration of 0.14 M and 1 mol % of catalyst. Reactions were complete during 3 hours. #Determined by enantiodiscriminating GC. * The absolute configuration was assigned by comparison of the sign of optical rotation with reported data.

EXAMPLE C

Hydrogenation of itaconic acid and dimethyl itaconate, respectively, using an isolated pre-catalyst [Rh(Ligand)(cod)]SbF$_6$ (with cis-PEP, trans-PEP, (S$_P$,R,R)-Me-PEP and (S$_P$,R,S)-Me-PEP as the Ligands).

TABLE C

| Substrate | Ligand | Solvent | % conv.# | % ee# (conf.)* |
|---|---|---|---|---|
| 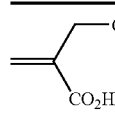 | (Sp, S)-cis-PEP | MeOH | 100 | 71 (S) |
| | (Sp, R)-trans-PEP | MeOH | 100 | 52 (S) |
| | (Sp, R, R)-Me-PEP | MeOH | 100 | 71 (S) |
| | (Sp, R, R)-Me-PEP | THF | 100 | 87 (S) |
| | (Sp, R, S)-Me-PEP | THF | 100 | 55 (S) |
| 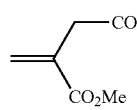 | (Sp, S)-cis-PEP | MeOH | 100 | 77 (S) |
| | (Sp, R)-trans-PEP | MeOH | 100 | 50 (S) |
| | (Sp, S)-cis-PEP | THF | 100 | 70 (S) |
| | (Sp, R)-trans-PEP | THF | 100 | 72 (S) |
| | (Sp, R, R)-Me-PEP | MeOH | 100 | 85 (S) |
| | (Sp, R, R)-Me-PEP | THF | 100 | 90 (S) |
| | (Sp, R, S)-Me-PEP | THF | 100 | 63 (S) |

All reactions were performed at room temperature with a substrate concentration of 0.14M and 1 mol % of catalyst. Reactions were complete during 3 hours.
Determined by enantiodiscriminating GC.
*The absolute configuration was assigned by comparison of the sign of optical rotation with reported data.

All reactions were performed at room temperature with a substrate concentration of 0.14 M and 1 mol % of catalyst. Reactions were complete during 3 hours. #Determined by enantiodiscriminating GC. * The absolute configuration was assigned by comparison of the sign of optical rotation with reported data.

EXAMPLE D

Hydrogenation of ethyl α-acetoxyacrylate and diethyl 1-benzylamino-1-ethanephosphonate, respectively, using an isolated pre-catalyst [Rh(Ligand)(cod)]SbF$_6$ (with cis-PEP, trans-PEP, (S$_P$,R,R)-Me-PEP and (S$_P$,R,S)-Me-PEP as the Ligands).

TABLE D

| Substrate | Ligand | Solvent | % conv.# | % ee# (conf.)* |
|---|---|---|---|---|
| 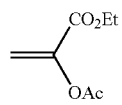 | (Sp, S)-cis-PEP | MeOH | 100 | 53 (R) |
| | (Sp, R)-trans-PEP | MeOH | 99 | 7 (R) |
| | (Sp, R, R)-Me-PEP | THF | 98 | 32 (S) |
| | (Sp, R, S)-Me-PEP | THF | 94 | 15 (R) |
| 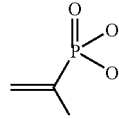 | (Sp, S)-cis-PEP | MeOH | 100 | 34 (nd) |
| | (Sp, R)-trans-PEP | MeOH | 100 | 19 (nd) |
| | (Sp, R, R)-Me-PEP | THF | 100 | 20 (nd) |
| | (Sp, R, S)-Me-PEP | THF | 100 | 30 (nd) |

All reactions were performed at room temperature with a substrate concentration of 0.14M and 1 mol % of catalyst. Reactions were complete during 3 hours.
Determined by enantiodiscriminating GC.
*The absolute configuration was assigned by comparison of the sign of optical rotation with reported data.

All reactions were performed at room temperature with a substrate concentration of 0.14 M and 1 mol % of catalyst. Reactions were complete during 3 hours. #Determined by enantiodiscriminating GC. * The absolute configuration was assigned by comparison of the sign of optical rotation with reported data.

EXAMPLE E

Hydrogenation of acetophenone N-benzoylhydrazone and α-(acetylamino)-β,β-dimethylacrylic acid, respectively, using an isolated pre-catalyst [Rh(Ligand)(cod)]SbF$_6$ (with cis-PEP, trans-PEP, (S$_P$,R,R)-Me-PEP and (S$_P$,R,S)-Me-PEP as the Ligands).

TABLE E

| Substrate | Ligand | Solvent | % conv.# | % ee# (conf.)* |
|---|---|---|---|---|
| 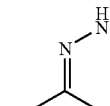 | (Sp, S)-cis-PEP | MeOH | 40^ | 29^ (S) |
| | (Sp, R)-trans-PEP | THF | 100^ | 46^ (S) |
| | (Sp, R, R)-Me-PEP | THF | 99^ | 55^ (S) |
| | (Sp, R, S)-Me-PEP | THF | 99^ | 50^ (S) |
| 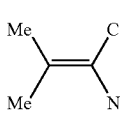 | (Sp, S)-cis-PEP | MeOH | 100 | 64 (S) |
| | (Sp, R)-trans-PEP | THF | 100 | <1 (R) |
| | (Sp, R, R)-Me-PEP | THF | 100 | 33 (R) |
| | (Sp, R, S)-Me-PEP | THF | 100 | 36 (S) |

All reactions were performed at room temperature with a substrate concentration of 0.14M and 1 mol % of catalyst. Reactions were complete during 3 hours.
Determined by enantiodiscriminating GC.
^Determined by enantiodiscriminating HPLC.
*The absolute configuration was assigned by comparison of the sign of optical rotation with reported data.

All reactions were performed at room temperature with a substrate concentration of 0.14 M and 1 mol % of catalyst. Reactions were complete during 3 hours. #Determined by enantiodiscriminating GC. * The absolute configuration was assigned by comparison of the sign of optical rotation with reported data.

EXAMPLE F

Hydrogenation of α-acetamidoacrylic acid and methyl α-acetamidoacrylate, respectively, using an isolated pre-catalyst [Rh(Ligand)(cod)]BF$_4$ (with cis-PEP and trans-PEP as the Ligands).

TABLE F

| Substrate | Ligand | % conv.# | % ee# (conf.)* |
|---|---|---|---|
| 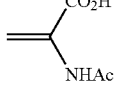 | (Sp, S)-cis-PEP | 100 | 22 (S) |
| | (Sp, R)-trans-PEP | 100 | <1 (S) |
| 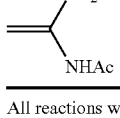 | (Sp, S)-cis-PEP | 100 | 28 (S) |
| | (Sp, R)-trans-PEP | 100 | 9 (R) |

All reactions were performed at room temperature with a substrate concentration of 0.14M in methanol and 1 mol % of catalyst. Reactions were complete during 3 hours.
Determined by enantiodiscriminating GC.
*The absolute configuration was assigned by comparison of the sign of optical rotation with reported data.

All reactions were performed at room temperature with a substrate concentration of 0.14 M and 1 mol % of catalyst. Reactions were complete during 3 hours. #Determined by enantiodiscriminating GC. * The absolute configuration was assigned by comparison of the sign of optical rotation with reported data.

EXAMPLE G

Hydrogenation of methyl α-acetamidocinnamate and ethyl α-acetoxyacrylate, respectively, using an isolated pre-catalyst [Rh(Ligand)(cod)]BF$_4$ (with cis-PEP and trans-PEP as the Ligands).

TABLE G

| Substrate | Ligand | % conv.# | % ee# (conf.)* |
|---|---|---|---|
| Ph—C(CO$_2$Me)=CH—NHAc | (Sp, S)-cis-PEP | 100 | 13 (S) |
| | (Sp, R)-trans-PEP | 100 | 25 (S) |
| CH$_2$=C(CO$_2$Et)—OAc | (Sp, S)-cis-PEP | 99 | 54 (R) |
| | (Sp, R)-trans-PEP | 99 | 7 (R) |

All reactions were performed at room temperature with a substrate concentration of 0.14M in methanol and 1 mol % of catalyst. Reactions were complete during 3 hours.
Determined by enantiodiscriminating GC.
*The absolute configuration was assigned by comparison of the sign of optical rotation with reported data.

All reactions were performed at room temperature with a substrate concentration of 0.14 M and 1 mol % of catalyst. Reactions were complete during 3 hours. #Determined by enantiodiscriminating GC. * The absolute configuration was assigned by comparison of the sign of optical rotation with reported data.

EXAMPLE H

Hydrogenation of itaconic acid and dimethyl itaconate, respectively, using an isolated pre-catalyst [Rh(Ligand)(cod)]SbF$_6$ (with cis-PEP and trans-PEP as the Ligands).

TABLE H

| Substrate | Ligand | % conv.# | % ee# (conf.)* |
|---|---|---|---|
| CH$_2$=C(CO$_2$H)—CH$_2$—CO$_2$H | (Sp, S)-cis-PEP | 100 | 58 (S) |
| | (Sp, R)-trans-PEP | 100 | 49 (S) |
| CH$_2$=C(CO$_2$Me)—CH$_2$—CO$_2$Me | (Sp, S)-cis-PEP | 100 | 57 (S) |
| | (Sp, R)-trans-PEP | 100 | 50 (S) |

All reactions were performed at room temperature with a substrate concentration of 0.14M in methanol and 1 mol % of catalyst. Reactions were complete during 3 hours.
Determined by enantiodiscriminating GC.
*The absolute configuration was assigned by comparison of the sign of optical rotation with reported data.

All reactions were performed at room temperature with a substrate concentration of 0.14 M and 1 mol % of catalyst. Reactions were complete during 3 hours. #Determined by enantiodiscriminating GC. * The absolute configuration was assigned by comparison of the sign of optical rotation with reported data.

EXAMPLE I

Hydrogenation of dimethyl itaconate using [Rh(cod)(S$_P$, R)-(trans-PEP)]BARF as the pre-catalyst.

TABLE I

| Substrate | Solvent | % conv.# | % ee# (conf.)* |
|---|---|---|---|
| CH$_2$=C(CO$_2$Me)—CH$_2$—CO$_2$Me | MeOH | 100 | 50 (S) |
| | THF | 100 | 72 (S) |
| | CH$_2$Cl$_2$ | 100 | 65 (S) |
| | Toluene | 79 | 22 (S) |
| | EtOAc | 100 | 70 (S) |

All reactions were performed at room temperature with a substrate concentration of 0.14M and 1 mol % of catalyst. Reactions were complete during 3 hours.
Determined by enantiodiscriminating GC.
*The absolute configuration was assigned by comparison of the sign of optical rotation with reported data.

All reactions were performed at room temperature with a substrate concentration of 0.14 M and 1 mol % of catalyst. Reactions were complete during 3 hours. #Determined by enantiodiscriminating GC. * The absolute configuration was assigned by comparison of the sign of optical rotation with reported data.

What is claimed is:
1. A Compound of formula I

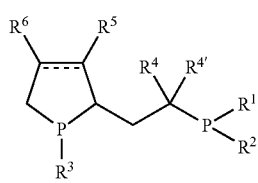

wherein
R$^1$ and R$^2$ are independently selected from the group consisting of alkyl, aryl, or cycloalkyl, said alkyl, aryl, or cycloalkyl being unsubstituted or substituted by alkyl, alkoxy, halogen, amino, hydroxy, amino, mono- or dialkylamino, aryl, —SO$_2$—R$^7$, —SO$_3^-$, —CO—NR$^8$R$^{8'}$, carboxy, alkoxycarbonyl, trialkylsilyl, diarylalkylsilyl, dialkylarylsilyl or triarylsilyl;
R$^3$ is selected from the group consisting of alkyl, cycloalkyl, and aryl;
R$^{4'}$ and R$^4$ are independently selected from the group consisting of hydrogen, alkyl and aryl; or
R$^{4'}$ and R$^4$ together with the C-atom they are attached to form a 3-8-membered carbocyclic ring;
the dotted line is absent or is present and forms a double bond;
R$^5$ and R$^6$ are independently selected from the group consisting of hydrogen, alkyl and aryl;
R$^7$ is selected from the group consisting of alkyl, aryl and NR$^8$R$^{8'}$; and
R$^8$ and R$^{8'}$ are independently selected from the group consisting of hydrogen, alkyl and aryl.
2. The Compound of claim 1, said compound having a formula selected from the group consisting of

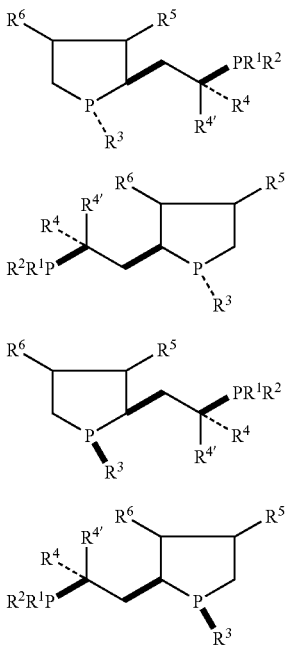

wherein $R^1, R^2, R^3, R^4, R^{4'}, R^5, R^6, R^7$ and $R^8$ are as defined in claim 1.

3. A compound of claim 2, said compound have a formula selected from the group consisting of

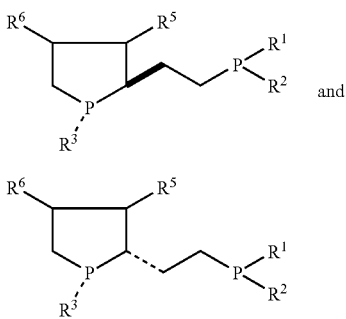

wherein $R^1, R^2, R^3, R^5, R^6, R^7, R^8$ and $R^{4'}$ are as defined in claim 1.

4. A compound of claim 2 wherein
$R^1$ and $R^2$ are alike and signify alkyl, aryl, or cycloalkyl, said alkyl, aryl, or cycloalkyl being unsubstituted or substituted by alkyl, alkoxy, halogen, hydroxy, amino, mono- or dialkylamino, aryl, $-SO_2-R^7$, $-SO_3^-$, $-CO-NR^8R^{8'}$, carboxy, alkoxycarbonyl, trialkylsilyl, diarylalkylsilyl, dialkylarylsilyl or triarylsilyl;
$R^3$ is $C_{1-4}$ alkyl or aryl;
$R^{4'}$ and $R^4$ are independently selected from the group consisting of hydrogen, $C_{1-4}$ alkyl and aryl;
$R^5$ and $R^6$ are independently selected from the group consisting of hydrogen, $C_{1-4}$ alkyl and phenyl;
$R^7, R^8$ and $R^{8'}$ are as defined in claim 1
and the dotted line is absent.

5. A compound of claim 4, wherein
$R^1$ and $R^2$ are aryl;
$R^3$ is tert-butyl or phenyl;
$R^{4'}$ and $R^4$ are independently selected from the group consisting of hydrogen, $C_{1-4}$ alkyl and aryl;
$R^5$ and $R^6$ are hydrogen
and the dotted line is absent.

6. A compound of claim 4, wherein
$R^1$ and $R^2$ are aryl;
$R^3$ is phenyl;
$R^4, R^{4'}$ are independently selected from the group consisting of hydrogen, methyl and phenyl;
$R^5$ and $R^6$ are hydrogen;
and the dotted line is absent.

7. A compound of claim 5, wherein
$R^1$ and $R^2$ are phenyl;
$R^3$ is phenyl;
$R^4, R^{4'}$ are selected from the group consisting of hydrogen, methyl and phenyl;
$R^5$ and $R^6$ are hydrogen;
and the dotted line is absent.

8. A compound of claim 3, wherein
$R^1$ and $R^2$ are alike and are selected from the group consisting of alkyl, aryl, and cycloalkyl, said alkyl, aryl, or cycloalkyl being unsubstituted or substituted by alkyl, alkoxy, halogen, hydroxy, amino, mono- or dialkylamino, aryl, $-SO_2-R^7$, $-SO_3^-$, $-CO-NR^8R^{8'}$, carboxy, alkoxycarbonyl, trialkylsilyl, diarylalkylsilyl, dialkylarylsilyl or triarylsilyl;
$R^3$ is $C_{1-4}$ alkyl or aryl;
$R^5$ and $R^6$ are independently selected from the group consisting of hydrogen, $C_{1-4}$ alkyl and phenyl;
the dotted line is absent; and
$R^7, R^8$ and $R^{8'}$ are as defined in claim 1.

9. A compound of claim 8, wherein
$R^1$ and $R^2$ are alike and are aryl;
$R^3$ is tert-butyl or phenyl;
$R^5$ and $R^6$ are hydrogen;
and the dotted line is absent.

10. A compound of claim 9, wherein
$R^1$ and $R^2$ are alike and signify phenyl;
$R^3$ is phenyl;
$R^5$ and $R^6$ are hydrogen;
and the dotted line is absent.

11. A compound of claim 1, which compounds are selected from the group consisting of
($S_P$,R)-trans-2-(2-diphenylphosphino)ethyl-1-phenylphospholane;
(S,S)-cis-2-(2-diphenylphosphino)ethyl-1-phenylphospholane;
($S_P$,R,R)-trans-2-(2-diphenylphosphino-2-methyl)ethyl-1-phenylphospholane;
($S_P$,R,S)-trans-2-(2-diphenylphosphino-2-methyl)ethyl-1-phenylphospholane;
($R_P$,R,R)-cis-2-(2-diphenylphosphino-2-methyl)ethyl-1-phenylphospholane;
($R_P$,R,S)-cis-2-(2-diphenylphosphino-2-methyl)ethyl-1-phenylphospholane;
($S_P$,R,R)-trans-2-(2-diphenylphosphino-2-phenyl)ethyl-1-phenylphospholane;
($S_P$,R,S)-trans-2-(2-diphenylphosphino-2-phenyl)ethyl-1-phenylphospholane;
($R_P$,R,R)-cis-2-(2-diphenylphosphino-2-phenyl)ethyl-1-phenylphospholane; and
($R_P$,R,S)-cis-2-(2-diphenylphosphino-2-phenyl)ethyl-1-phenylphospholane; or the enantiomers of these compounds.

* * * * *